(12) United States Patent
Pascual et al.

(10) Patent No.: US 8,241,863 B2
(45) Date of Patent: Aug. 14, 2012

(54) IDENTIFICATION OF AN EVOLUTIONARILY CONSERVED PATHWAY MEDIATING TRANSREPRESSION OF INFLAMMATORY RESPONSE GENES BY NUCLEAR RECEPTORS

(75) Inventors: Gabriel Pascual, San Diego, CA (US); Christopher K. Glass, San Diego, CA (US); Michael G. Rosenfeld, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 684 days.

(21) Appl. No.: 11/886,057

(22) PCT Filed: Mar. 10, 2006

(86) PCT No.: PCT/US2006/008905
§ 371 (c)(1), (2), (4) Date: Sep. 10, 2007

(87) PCT Pub. No.: WO2006/104678
PCT Pub. Date: Oct. 5, 2006

(65) Prior Publication Data
US 2008/0182778 A1 Jul. 31, 2008

Related U.S. Application Data

(60) Provisional application No. 60/661,054, filed on Mar. 10, 2005.

(51) Int. Cl.
*G01N 33/53* (2006.01)
(52) U.S. Cl. ......................................... 435/7.8
(58) Field of Classification Search ........................ None
See application file for complete search history.

(56) References Cited

U.S. PATENT DOCUMENTS

2004/0253648 A1 12/2004 Fletterick et al.
2005/0202440 A1* 9/2005 Fletterick et al. ................. 435/6

OTHER PUBLICATIONS

Hauser et al. (2000) J. Biol. Chem. 275: 18527-18533.*
Poukka et al. (2000) PNAS 97: 14145-14150.*
Auphan, Nathalie et al., "Immunosuppression by Glucocorticoids: Inhibition of NF-κB Activity Through Induction of IκB Synthesis," *Science*, 1995, 270:286-90.
Bosscher, Karolien De et al., "The Interplay between the Glucocorticoid Receptor and Nuclear Factor-κB or Activator Protein-1: Molecular Mechanisms for Gene Repression," *Endocrine Reviews*, 2003, 24:488-522.
Boutros, Michael et al., "Sequential Activation of Signaling Pathways during Innate Immune Responses in Drosophila," *Developmental Cell*, 2002, 3:711-22.
Chawla, Ajay et al., "A PPARγ-LXR-ABCA1 Pathway in Macrophages Is Involved in Cholesterol Efflux and Atherogenesis," *Molecular Cell*, 2001, 7:161-71.
Chen, J. Don and Ronald M. Evans, "A transcriptional co-repressor that interacts with nuclear hormone receptors," *Nature*, 1995, 377:454-7.
Chen, Zhong et al., "Troglitazone inhibits Atherosclerosis in Apolipoprotein E-Knockout Mice; Pleiotropic Effects on CD36 Expression and HDL," *Arterioscler. Thromb. Vasc. Biol.*, 2001, 21:372-7.
Claudel, Thierry et al., "Reduction of atherosclerosis in apolipoprotein E knockout mice by activation of the retinoid X receptor," *PNAS*, 2001, 98:2610-5.
Collins, Alan R. et al., "Troglitazone Inhibits Formation of Early Atherosclerotic Lesions in Diabetic and Nondiabetic Low Density Lipoprotein Receptor-Deficient Mice," *Arterioscler. Thromb. Vasc. Biol.*, 2001, 21:365-71.
Gavrilova, Oksana et al., "Liver Peroxisome Proliferator-activated Receptor γ Contributes to Hepatic Steatosis, Triglyceride Clearance, and Regulation of Body Fat Mass," *The Journal of Biological Chemistry*, 2003, 278:34268-76.
Glass, Christopher K. and Michael G. Rosenfeld, "The coregulator exchange in transcriptional functions of nuclear receptors," *Genes & Development*, 2000, 14:121-41.
Guenther, Matthew G. et al., "A core SMRT corepressor complex containing HDAC3 and TBL1, a WD40-repeat protein linked to deafness," *Genes & Development*, 2000, 14:1048-57.
He, Weimin et al., "Adipose-specific peroxisome proliferator-activated receptor γ knockout causes insulin resistance in fat and liver but not in muscle," *PNAS*, 2003, 100:15712-7.
Hevener, Andrea L. et al., "Muscle-specific Pparg deletion causes insulin resistance," *Nature Medicine*, 2003, 9:1491-7.
Hoberg, Jamie E. et al., "SMRT Derepression by the IκB Kinase α: A Prerequisite to NF-κB Transcription and Survival," *Molecular Cell*, 2004, 16:245-55.
Hörlein, Andreas J. et al., "Ligand-independent repression by the thyroid hormone receptor mediated by a nuclear receptor co-repressor," *Nature*, 1995, 377:397-403.
Ito, Kazuhiro et al., "Glucocorticoid Receptor Recruitment of Histone Deacetylase 2 Inhibits Interleukin-1β-Induced Histone H4 Acetylation of Lysines 8 and 12," *Molecular and Cellular Biology*, 2000, 20:6891-903.
Jackson, Peter K., "A new RING for SUMO: wrestling transcriptional responses into nuclear bodies with PIAS family E3 SUMO ligases," *Genes & Development*, 2001, 15:3053-8.
Jänne, O. A. et al., "Androgen-receptor-interacting nuclear proteins," *Biochemical Society Transactions*, 2000, 28:401-5.
Jiang, Chengyu et al., "PPAR-γ agonists inhibit production of monocyte inflammatory cytokines," *Nature*, 1998, 391:82-6.
Jonat, Carsten et al., "Antitumor Promotion and Antiinflammation: Down-Modulation of AP-1 (Fos/Jun) Activity by Glucocorticoid Hormone," *Cell*, 1990, 62:1189-204.

(Continued)

*Primary Examiner* — Michael Pak
(74) *Attorney, Agent, or Firm* — Adriano & Associates

(57) ABSTRACT

The present invention relates to a method of screening for a compound that regulate SUMOylation of the nuclear receptor proteins comprising contacting the compound of interest to the nuclear receptor protein, and detecting SUMOylation of the nuclear receptor protein, thereby screening for a compound that regulates SUMOylation.

6 Claims, 19 Drawing Sheets

OTHER PUBLICATIONS

Kirkpatrick, Robert B. et al., "An abundantly secreted glycoprotein from *Drosophila melanogaster* is related to mammalian secretory proteins produced in rheumatoid tissues and by activated macrophages," *Gene*, 1995, 153:147-54.

Kotaja, Noora et al., "PIAS Proteins Modulate Transcription Factors by Functioning as SUMO-1 Ligases," *Molecular and Cellular Biology*, 2002, 22:5222-34.

Kuhlencordt, Peter J. et al., "Genetic Deficiency of Inducible Nitric Oxide Synthase Reduces Atherosclerosis and Lowers Plasma Lipid Peroxides in Apolipoprotein E-Knockout Mice," *Circulation*, 2001, 103:3099-104.

Lehmann, Jürgen M. et al., "An Antidiabetic Thiazolidinedione Is a High Affinity Ligand for Peroxisome Proliferator-activated Receptor γ (PPARγ)," *The Journal of Biological Chemistry*, 1995, 270:12953-6.

Li, Andrew C. et al., "Peroxisome proliferatator-activated receptor γ ligands inhibit development of atherosclerosis in LDL receptor-deficient mice," *The Journal of Clinical Investigation*, 2000, 106:523-31.

Li, Jiwen et al., "Both corepressor proteins SMRT and N-CoR exist in large protein complexes containing HDAC3," *The EMBO Journal*, 2000, 19:4342-50.

Ling, Yan et al., "Modification of de novo DNA methyltransferase 3a (Dnmt3a) by SUMO-1 modulates its interaction with histone deacetylases (HDACs) and its capacity to repress transcription," *Nucleic Acids Research*, 2004, 32:598-610.

Liu, Bin et al., "Inhibition of Stat1-mediated gene activation by PIAS1," *Proc. Natl. Acad. Sci. USA*, 1998, 95:10626-31.

Lowenstein, Charles J. et al., "Macrophage nitric oxide synthase gene: Two upstream regions mediate induction by interferon γ and lipopolysaccharide," *Proc. Natl. Acad. Sci. USA*, 1993, 90:9730-4.

Müller, Stefan et al., "SUMO, Ubiquitin's Mysterious Cousin," *Nature Reviews*, 2001, 2:202-10.

Nishida, Tamotsu and Hideyo Yasuda, "PIAS1 and PIASxα Function as SUMO-E3 Ligases toward Androgen Receptor and Repress Androgen Receptor-dependent Transcription," *The Journal of Biological Chemistry*, 2002, 277:41311-7.

Nissen, Robert M. and Keith R. Yamamoto, "The glucocorticoid receptor inhibits NFκB by interfering with serine-2 phosphorylation of the RNA polymerase II carboxy-terminal domain," *Genes & Development*, 2000, 14:2314-29.

Norris, Andrew W. et al., "Muscle-specific PPARγ-deficient mice develop increased adiposity and insulin resistance but respond to thiazolidinediones," *The Journal of Clinical Investigation*, 2003, 112:608-18.

Oberfield, Jennifer L. et al., "A peroxisome proliferator-activated receptor γ ligand inhibits adipocyte differentiation," *Proc. Natl. Acad. Sci. USA*, 1999, 96:6102-6.

Ogawa, Sumito et al., "A nuclear receptor corepressor transcriptional checkpoint controlling activator protein 1-dependent gene networks required for macrophage activation," *PNAS*, 2004, 101:14461-6.

Ohshima, Takayuki et al., "Transcriptional Activity of Peroxisome Proliferator-activated Receptor γ Is Modulated by SUMO-1 Modification," *The Journal of Biological Chemistry*, 2004, 279:29551-7.

Perissi, Valentina et al., "A Corepressor/Coactivator Exchange Complex Required for Transcriptional Activation by Nuclear Receptors and Other Regulated Transcription Factors," *Cell*, 2004, 116:511-26.

Perreault, Mylène and André Marette, "Targeted disruption of inducible nitric oxide synthase protects against obesity-linked insulin resistance in muscle," *Nature Medicine*, 2001, 7:1138-43.

Picard, Frédéric and Johan Auwerx, "PPARγ and Glucose Homeostasis," *Annu. Rev. Nutr.*, 2002, 22:167-97.

Pittas, Anastassios G. et al., "Adipocytokines and Insulin Resistance," *The Journal of Clinical Endocrinology & Metabolism*, 2004, 89:447-52.

Ricote, Mercedes et al., "The peroxisome proliferator-activated receptor-γ is a negative regulator of macrophage activation," *Nature*, 1998, 391:79-82.

Schneider, Imogene, "Cell lines derived from late embryonic stages of *Drosophila melanogaster*," *J. Embryol. Exp. Morph.*, 1972, 27:353-65.

Schüle, Roland et al., "Functional Antagonism between Oncoprotein c-Jun and Glucocorticoid Receptor," *Cell*, 1990, 62:1217-26.

Sheppard, Kelly-Ann et al., "Nuclear Integration of Glucocorticoid Receptor and Nuclear Factor-κB Signaling by CREB-binding Protein and Steroid Receptor Coactivator-1," *The Journal of Biological Chemistry*, 1998, 273:29291-4.

Spiegelman, B.M., "PPAR-: Adipogenic Regulator and Thiazolidinedione Receptor," *Diabetes*, 1998, 47:507-14.

Tallec, Laurent Pascual-Le et al., "Protein Inhibitor of Activated Signal Transducer and Activator of Transcription 1 Interacts with the N-Terminal Domain of Mineralocorticoid Receptor and Represses Its Transcriptional Activity: Implication of Small Ubiquitin-Related Modifier 1 Modification," *Molecular Endocrinology*, 2003, 17:2529-42.

Tan, Jiann-an et al., "Protein Inhibitor of Activated STAT-1 (Signal Transducer and Activator of Transcription-1) Is a Nuclear Receptor Coregulator Expressed in Human Testis," *Molecular Endocrinology*, 2000, 14:14-26.

Tontonoz, Peter et al., "PPARγ Promotes Monocyte/Macrophage Differentiation and Uptake of Oxidized LDL," *Cell*, 1998, 93:241-52.

Weisberg, Stuart P. et al. "Obesity is associated with macrophage accumulation in adipose tissue," *The Journal of Clinical Investigation*, 2003, 112:1796-808.

Welch, John S. et al., "PPARγ and PPARδ negatively regulate specific subsets of lipopolysaccharide and IFN-γ target genes in macrophages," *PNAS*, 2003, 100:6712-7.

Willson, Timothy M. et al., "The Structure-Activity Relationship between Peroxisome Proliferator-Activated Receptor γ Agonism and the Antihyperglycemic Activity of Thiazolidinediones," *Journal of Medicinal Chemistry*, 1996, 39:665-8.

Xu, Haiyan et al., "Chronic inflammation in fat plays a crucial role in the development of obesity-related insulin resistance," *The Journal of Clinical Investigation*, 112:1821-30, 2003.

Yang-Yen, Hsin-Fang et al., "Transcriptional Interference between c-Jun and the Glucocorticoid Receptor: Mutual Inhibition of DNA Binding Due to Direct Protein-Protein Interaction," *Cell*, 1990, 62:1205-15.

Yoon, Ho-Geun et al., "Purification and functional characterization of the human N-CoR complex: the roles of HDAC3, TBL1 and TBLR1," *The EMBO Journal*, 2003, 22:1336-46.

Zhang, Jinsong et al., "The N-CoR-HDAC3 Nuclear Receptor Corepressor Complex Inhibits the JNK Pathway through the Integral Subunit GPS2," *Molecular Cell*, 2002, 9:611-23.

\* cited by examiner

9

| | IP Anti-HA-PPAR-γ | | |
|---|---|---|---|
| FL-PIAS1 | − | + | + |
| HA-PPAR-γ | − | + | + |
| Ro (min) | − | 0 | 30 |
| B: Anti-FL-PIAS1 | | | |
| B: Anti-HA-PPAR-γ | | | |

| | IP Anti-PPAR-γ | |
|---|---|---|
| Ro (min) | 0 | 30 |
| B: Anti-PIAS1 | | |
| B: Anti-PPAR-γ | | |
| 5% Input: PPAR-γ | | |
| 5% Input: PIAS1 | | |

Legend:
22R: 22(R)-HC (hydroxycholesterol)
22S: 22(S)-HC (hydroxycholesterol)
EC: 24(S),25-EC (epoxycholesterol)
24-HC: 24-HC (hydroxycholesterol)
25-HC: 25-HC (hydroxycholesterol)
27-HC: 27-HC (hydroxycholesterol)

US 8,241,863 B2

IDENTIFICATION OF AN EVOLUTIONARILY CONSERVED PATHWAY MEDIATING TRANSREPRESSION OF INFLAMMATORY RESPONSE GENES BY NUCLEAR RECEPTORS

This application is a 371 application of PCT application No. PCT/US2006/008905, filed Mar. 10, 2006, which claims the priority of U.S. Ser. No. 60/661,054, filed Mar. 10, 2005, the contents of all of which are hereby incorporated by reference in their entirety into the present application.

This invention was made with government support under Grant No. CA52599 awarded by the National Institute of Health. The government has certain rights to this invention.

Throughout this application various publications are referenced. The disclosures of these publications in their entireties are hereby incorporated by reference into this application in order to more fully describe the state of the art to which the invention pertains.

BACKGROUND OF THE INVENTION

Many nuclear receptor proteins act in trans to repress transcriptional responses to signaling pathways as a central aspect of their biological functions, but the underlying mechanisms remain an important and unresolved question in development and homeostasis.

The peroxisome proliferator-activated receptor γ (PPARγ) plays essential roles in fat cell development and glucose homeostasis. Further, PPARγ is the molecular target of insulin-sensitizing drugs, including rosiglitazone and other thiazolidinediones (TZDs)[2,3] that improve insulin resistance by regulating the actions of PPARγ in several tissues[4-8]. PPARγ is thought to improve insulin resistance by both positively and negatively regulating gene expression, with PPARγ agonists suppressing the expression of inflammatory genes in adipocytes and adipose tissue-associated macrophages that are correlated with impaired insulin signaling[9-11]. PPARγ agonists have also been demonstrated to inhibit the development of atherosclerosis in animal models and to reduce the expression of inflammatory mediators within atherosclerotic lesions[12-16]. Gene expression profiling experiments suggest that transrepression is the primary transcriptional function of PPARγ in macrophages[17]. Although the ability of PPARγ and other nuclear receptor proteins to negatively regulate inflammatory gene expression by antagonizing the actions of NF-κB and AP-1 has been extensively studied[18-26] (and reviewed in[27]), the molecular mechanisms remain poorly understood. Transrepression by PPARγ requires both its ligand binding and DNA binding domains, but not sequence-specific DNA recognition[28]. Consistent with this, genes that are subject to transrepression do not typically contain consensus recognition sites for PPAR/RXR heterodimers that mediate ligand-dependent activation of positively regulated genes. Furthermore, heterodimerization with RXR does not appear to be required, because PPARγ retains transrepression activity in macrophages lacking RXRα, the major RXR isoform in these cells.

The nuclear receptor corepressor, NCoR, and the related factor, SMRT, are components of corepressor complexes containing HDAC3, TBL1 and TBLR1 that interact with a subset of unliganded nuclear receptor proteins and mediate active transcriptional repression[29-35]. The TBL1 and TBLR1 components contribute to stability of binding to chromatin through histone interactions, while the HDAC3 component contributes to active repression[35]. Binding of nuclear receptor agonists results in the exchange of NCoR/SMRT complexes for coactivator complexes and a consequent switch in receptor function from transcriptional repression to activation[32-34]. TBLR1 also appears to play critical roles in the dismissal of NCoR complexes from nuclear receptor target genes by recruiting a Ubc5-containing ubiquitylation/19S proteosome complex[36]. Recent studies have extended the biological roles of NCoR/HDAC3/TBL complexes to NF-κB and AP-1 target genes, where they function to maintain inflammatory-response genes in a repressed state in the absence of inductive signals[36-38].

The findings herein reveal a previously unrecognized molecular mechanism by which ligands regulate the transcriptional activities of nuclear receptors. This mechanism provides the basis for new screening strategies for the identification of novel classes of ligands that more effectively or more selectively activate anti-inflammatory actions of PPARs and other nuclear receptors. Such compounds would potentially represent improvements over existing drugs that exhibit significant side effects and/or suboptimal efficacy in inflammatory disease states including atherosclerosis and type II diabetes.

SUMMARY OF THE INVENTION

In general, the present invention provides methods of screening for compounds that regulate SUMOylation of a nuclear receptor protein.

The present invention provides a method of repressing inflammation comprising contacting a compound of interest with a nuclear receptor protein so as to activate SUMOylation of the nuclear receptor protein and thereby repressing inflammation.

The present invention also provides methods of screening for compounds that regulate SUMOylation of a nuclear receptor protein comprising contacting the compound of interest to the nuclear receptor protein and detecting SUMOylation of the nuclear receptor protein.

The present invention also provides methods of screening for a compound that regulate inflammation by activating SUMOylation of nuclear receptor proteins associated with inflammation comprising contacting the compound of interest to the nuclear receptor protein and detecting SUMOylation of the nuclear receptor protein.

The invention further provides a method of screening for a compound that regulates SUMOylation of the peroxisome proliferator-activated receptor comprising contacting a compound of interest to the peroxisome proliferator-activated receptor and detecting SUMOylation of peroxisome proliferator-activated receptor, thereby screening for a compound that regulates SUMOylation.

The invention also provides a method for determining whether a compound represses activation of inflammatory genes comprising (a) transfecting a cell with (i) a plasmid expressing a nuclear receptor protein, (ii) SUMO ligase siRNA or control siRNA, and (iii) an inflammation-responsive reporter gene, (b) contacting the transfected cell with the compound, and (c) assaying for compound dependent SUMOylation of the nuclear receptor protein by detecting transcriptional activation of a reporter gene, the activation of the reporter gene in the presence of SUMO ligase siRNA, but not in the presence of control siRNA, being indicative that the compound represses activation of inflammatory genes.

The invention further provides a method for determining whether a compound represses activation of inflammatory genes comprising contacting a cell expressing both, a corepressor protein joined to first label and nuclear receptor protein joined to second label, with the compound of interest, and assaying for the interaction of nuclear repressor protein and corepressor protein with each other by detecting transcriptional activation of a reporter gene having GAL4 binding sites, the activation of the reporter gene being indicative that the compound represses activation of inflammatory genes.

The invention also provides a method for inhibiting an immune response by SUMOylating a nuclear receptor protein, comprising contacting nuclear receptor protein positive cells with a compound that binds and activates SUMOylation of the nuclear receptor protein, thereby inhibiting an immune response.

The invention further provides a method of inhibiting an inflammatory response by SUMOylating a nuclear receptor protein, comprising contacting nuclear receptor protein positive cells with a compound that binds and activates SUMOylation of a nuclear receptor protein, thereby inhibiting an inflammatory response.

The present invention also provides a method for inhibiting expression of inflammatory genes comprising contacting nuclear receptor protein positive cells with a compound that binds and activates SUMOylation of the nuclear receptor protein, thereby inhibiting expression of inflammatory genes.

The invention also provides a use of a nuclear receptor protein for inhibiting an immune response by SUMOylating a nuclear receptor protein, comprising contacting the nuclear receptor protein positive cells with a compound that binds and activates SUMOylation of a nuclear receptor protein, thereby inhibiting an immune response.

The invention further provides a use of a nuclear receptor protein for inhibiting an inflammatory response by SUMOylating a nuclear receptor protein, comprising contacting the nuclear receptor protein positive cells with a compound that binds and activates SUMOylation of a nuclear receptor protein, thereby inhibiting an inflammatory response.

The present invention also provides a use of a nuclear receptor protein for inhibiting expression of inflammatory genes by SUMOylating a nuclear receptor protein, comprising contacting the nuclear receptor protein positive cells with a compound that binds and activates SUMOylation of the nuclear receptor protein, thereby inhibiting expression of inflammatory genes. The binding of a compound to the nuclear receptor protein activates SUMOylation of the nuclear receptor protein and represses inflammatory genes.

DETAILED DESCRIPTION OF THE INVENTION

Figure 1:
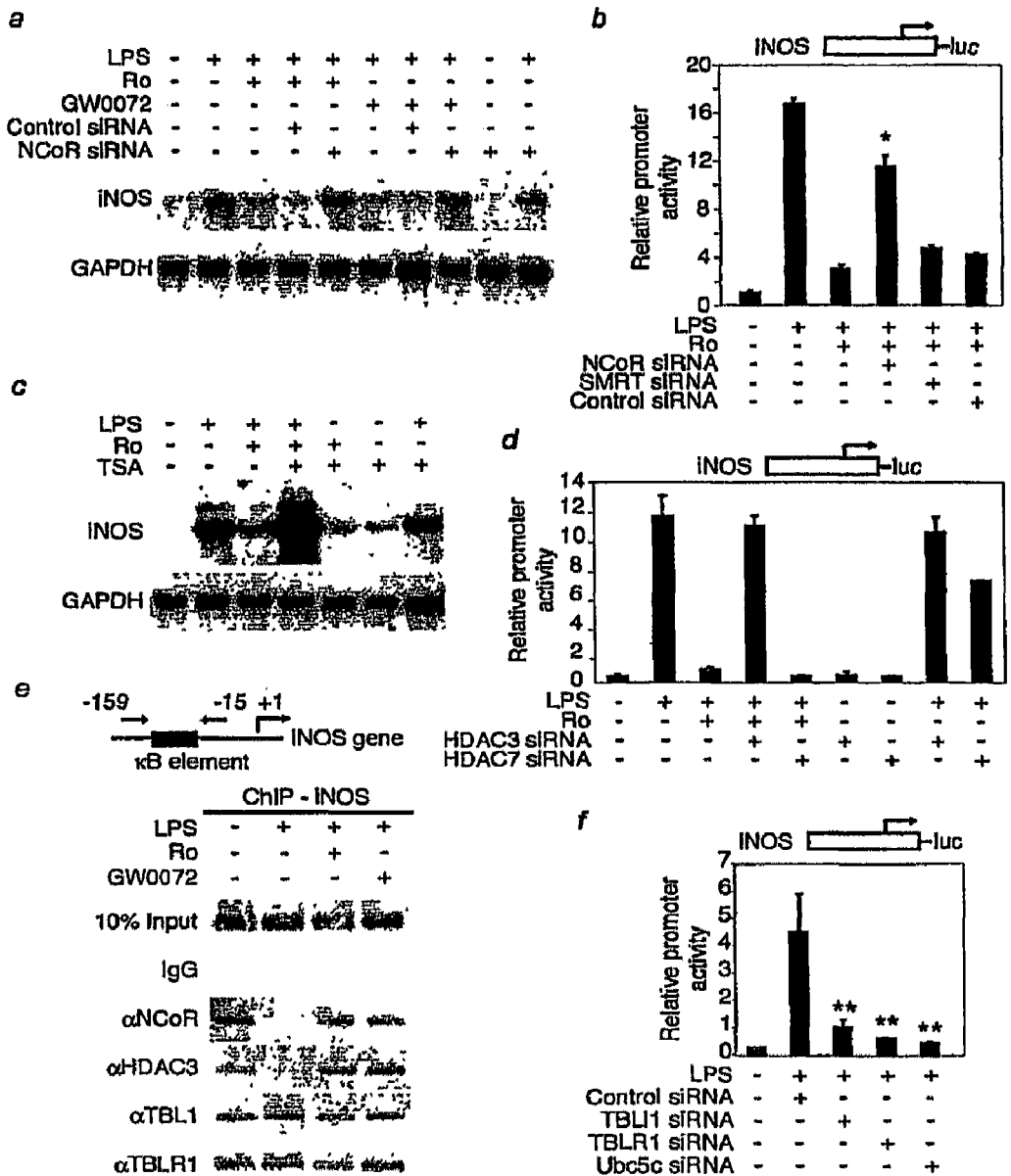
FIG. 1. Northern blot analysis (1a and 1c), luciferase gene activity (1b, 1d and 1f) and chromatin immunoprecipitaion (1e) show that PPARγ inhibits LPS induction of iNOS by an NCoR and HDAC3-dependent mechanism.
Figure 2:
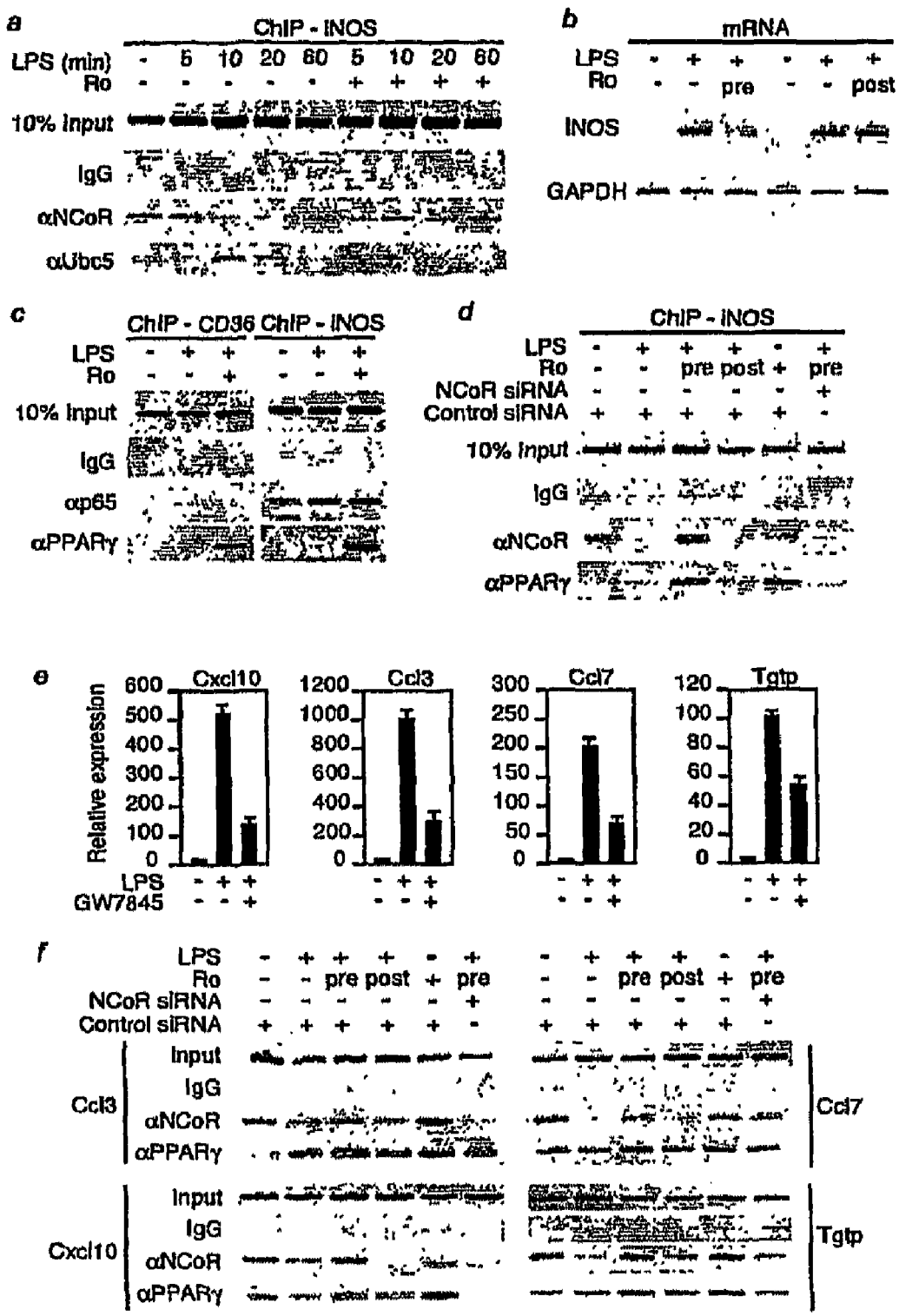
FIG. 2. Chromatin immunoprecipitation (2a, 2c, 2d and 2f), semi-quantitative RT-PCR (2b) and micro array analysis (2e) show that PPARγ targets NCoR corepressor complexes and prevents recruitment of UbcH15.

As used herein, the term "compound" or "ligand" refers to any chemical entity, pharmaceutical, drug, small molecule, proteins or portions thereof, peptide and the like, and/or combinations thereof, that specifically recognize and bind another molecule, that may or may not be used to treat or prevent a disease, illness, sickness, or disorder of bodily function.

As used herein, the term "therapeutic compounds" comprise both known and potential therapeutic compounds.

As used herein, the term "known therapeutic compound" refers to a compound that has been shown (e.g., through animal trials or prior experience with administration to humans) to be effective in such treatment or prevention.

As used herein, the term "therapeutic" when made in reference to a compound refers to a compound that is capable of reducing, delaying, or eliminating one or more undesirable pathologic effects in a subject.

As used herein, "administer" or "administering" means provided by any means including intravenous (i.v.) administration, intra-peritoneal (i.p.) administration, intramuscular (i.m.) administration, subcutaneous administration, oral administration, administration as a suppository, or as a topical contact, or the implantation of a slow-release device such as a miniosmotic pump, to the subject.

As used herein, "soluble" refers to any molecule, or fragments and derivatives thereof, not bound or attached to a cell, i.e., circulating.

As used herein, "oral," and "by oral administration" refers to the introduction of a pharmaceutical composition into a subject by way of the oral cavity (e.g. in aqueous liquid or solid form).

As used herein, "oral agent" refers to a compound that can be administered by way of the oral cavity (e.g. in aqueous liquid or solid form).

As used herein, the terms "subject" and "patient" refer to any animal, such as a mammal like a dog, cat, livestock, and a human (e.g. a human with a disease).

As used herein, the term "biological samples" refers to samples or specimens obtained from animals (including humans), and encompasses cells, fluids, solids, tissues, and gases. Biological samples include tissues (e.g., biopsy material), urine, cells, mucous, blood, and blood products such as plasma, serum and the like. However, these examples are not to be construed as limiting the types of samples that find use with the present invention.

As used herein, "buffer" refers to a chemical that neutralizes either acids or bases thus stabilizing pH (for example, sodium bicarbonate).

As used herein, NSAID refers to a Non-Steroidal Anti-Inflammatory Drug. NSAIDs reduce inflammatory reactions in a subject. NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tohnetin, acetaminophen, ibuprofen, Cox-2 inhibitors, meloxicam and tramadol.

As used herein, DMARD refers to a Disease Modifying Anti-Rheumatic Drug. A DMARD is any agent that modifies the symptoms and/or progression associated with an immune system disease, including autoimmune diseases (e.g. rheumatic diseases), graft-related disorders and immunoproliferative diseases. DMARDs include, but are not limited to, dihydrofolic acid reductase inhibitors e.g., methotrexate; cyclophosphamide; cyclosporine; cyclosporin A; chloroquine; hydroxychloroquine; sulfasalazine (sulphasalazopyrine) gold salts D-penicillamine; leflunomide; azathioprine; anakinra; TNF blockers e.g., infliximab (REMICADE®) or etanercept; and a biological agent that targets an inflammatory cytokine.

As used herein, to "block" or "inhibit" means to interfere with or prevent the binding to and/or activation of the receptor, signal or molecule.

As used herein, an "effective amount" of a molecule is defined as an amount that blocks and/or inhibits the interaction of a molecule with its ligand.

As used herein, "treating" a disease means to manage a disease by medicinal or other therapies. Treatment of a disease may ameliorate the symptoms of a disease, reduce the severity of a disease, alter the course of disease progression and/or ameliorate or cure the basic disease problem.

Examples of diseases wherein the compounds identified by the claimed methods may be used to inhibit an inflammatory response include immune disorders associated with graft transplantation rejection, chronic rejection, and tissue or cell allo- or xenografts, including solid organs (e.g., kidney transplants), skin, islets, muscles, hepatocytes, neurons, and graft versus host disease (GVHD) (e.g., such as may result from bone marrow transplantation, or in the induction of tolerance). Other examples of diseases include, but are not limited to, atherosclerosis, asthma, chronic obstructive pulmonary disease, psoriasis, T-cell lymphoma, T-cell acute lymphoblastic leukemia, testicular angiocentric T-cell lymphoma, benign lymphocytic angiitis, lupus (e.g. lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitis), good pasture's syndrome, myasthenia gravis, pemphigus, Crohn's disease, sympathetic ophthalnia, autoimmune uveitis, multiple sclerosis, Alzheimer's disease, Parkinson's disease, autoimmune hemolytic anemia, idiopathic thrombocytopenia, primary biliary cirrhosis, chronic active hepatitis, ulceratis colitis, Sjogren's syndrome, rheumatic diseases (e.g. rheumatoid arthritis), polymyositis, scleroderma, and mixed connective tissue disease.

As used herein, "rheumatic diseases" means any disease that affects the joints, bone, soft tissue, or spinal cord and comprises any of inflammatory rheumatism, degenerative rheumatism, extra-articular rheumatism, and collagen diseases. Additionally, rheumatic diseases include, but are not limited to, chronic polyarthritis, psoriasis arthropathica, ankylosing spondylitis, rheumatoid arthritis, panarteriitis nodosa, systemic lupus erythematosus, progressive systemic scleroderma, periarthritis humeroscapularis, arthritis uratica, chondrocalcinosis, dermatomyositis, muscular rheumatism, myositis, and myogelosis. Some rheumatic diseases are known to be autoimmune diseases caused by a subject's altered immune response.

As used herein, "alleviate" refers to lessening or making less severe, one or more of the symptoms of an immune disease.

As used herein, the term "IDC" refers to the extreme C terminus of NCoR.

As used herein, the term "nuclear receptor" or "nuclear receptor protein" refers to a protein that, upon binding of a ligand or when induced by a signal, specifically recognizes and binds to regulatory regions of DNA and modulates gene transcription and/or expression. Many nuclear receptor proteins are known in the art, such as androgen receptors, estrogen receptors, glucocorticoid receptors, peroxisome proliferators, thyroid receptors or vitamin D receptors.

As used herein, the term "nuclear receptor protein associated with inflammation" refers to a nuclear receptor protein that modulates the transcription and/or expression of an inflammatory gene.

Nuclear receptor proteins associated with inflammation of the present invention include, but are not limited to, PPARα, PPARγ, PPARδ, LXRα, LXRβ, vitamin D receptor, Nurr1, Nur77, Nor1, RXRα, and the like.

As used herein, the terms "modulate" or "regulate" when made in reference to gene transcription and expression means to "activate" or "repress" gene transcription and/or expression upon binding of a nuclear receptor protein to DNA. To "activate" gene transcription and/or expression means to regulate positively or up-regulate gene transcription and/or expression, whereas to "repress" means to regulate negatively and/or down-regulate gene transcription and expression.

As used herein, the term "inflammatory gene" refers to a gene that encodes a protein capable of promoting (pro-inflammatory gene) or inhibiting (anti-inflammatory gene) inflammation. Inflammatory genes are well known in the art and include, but are not limited to, NOS, COX, TNFα, IL1α, VCAM1, IFNγ, MCP-1, CCR2, resistin, or uteroglobin.

As used herein, the term "repressor" refers to a protein product of a regulator gene or a repressor gene, which acts to control transcription or expression of inducible and repressible genes. Generally, a repressor is any molecule that can reversibly inactivate a gene.

As used herein, the term "corepressor" refers to a molecule that combines with and activates a repressor, thus preventing gene transcription or expression. Repressors and corepressors can act as a single molecule or as a complex of two or more molecules.

As used herein, the term "SUMOylation" refers to the process of covalently coupling a small ubiquitin-like modifier, SUMO, to a molecule, e.g. protein. Conjugation of SUMO proteins to target substrates follows a three step pathway involving three enzymatic proteins termed E1, E2 and E3.

Macrophages cell lines include, but are not limited to, murine RAW264.7, human 28SC, human THP-1, human U937, human HB-8902, human CRL cell lines such as CRL-9850, CRL-9852, CRL-9853, CRL-9854, CRL-9855 and CRL-9856, rat NR8383 and the like.

In the experimental disclosure which follows, the following abbreviations apply: M (molar); mM (millimolar); μM (micromolar); nM (nanomolar); mol (moles); mmol (millimoles); μmol (micromoles); nmol (nanomoles); g (grams); mg (milligrams); μg (micrograms); pg (picograms); L (liters); mL (milliliters); ml (milliliters); μL (microliters); cm (centimeters); mm (millimeters); μm (micrometers); nm (nanometers); C (degrees Centigrade).

METHODS OF THE INVENTION

The present invention provides methods of screening for compounds (compounds of interest) that regulate SUMOylation of a nuclear receptor protein. The screening methods of the invention can involve direct or indirect detection of SUMOylation upon or after contacting a compound of interest with the nuclear receptor protein.

In one embodiment, when detection is effected using direct screening assays, the binding of the compound can be detected directly via SUMOylation of the nuclear receptor protein or interaction of nuclear receptor protein with a SUMO ligase, e.g., the contact between the nuclear receptor protein and SUMO, or the nuclear receptor protein and the SUMO E2 or E3 ligase.

Direct screenings may be performed by any technique for detecting of covalent or non covalent protein-protein interactions known in the art including, but not limited to, two-hybrid screens, fluorescence resonance energy transfer (FRET), enzyme-linked immunosorbent assay (ELISA), co-immunoprecipitation and Western blotting. In accordance with the methods of the invention, when assaying for protein-protein interaction, each or both of the assayed proteins, e.g., the nuclear receptor protein and SUMO, or the nuclear receptor protein and the SUMO ligase, may be modified by a fusion molecule, e.g. a fusion protein.

In an embodiment of the invention, when the method of detection is effected by fluorescence resonance energy transfer (FRET), the fluorescent dye may be a fluorescent protein such as the green fluorescent protein (GFP) and mutants or derivatives thereof, such as ECFP or EYFP.

Enzyme-linked immunosorbent assay (ELISA), co-immunoprecipitation and Western blotting may include the use of antibodies. Antibodies (portion or derivative or fragments thereof) may be monoclonal or polyclonal and may bind the nuclear receptor proteins, the SUMO ligases, the components of the co-repressor complex, and/or the components of the SUMOylation machinery. Examples of antibodies include but are not limited to antibodies that bind PIAS1, PPARγ, NCoR, HA-PPARγ, FLAG-LXRα, Myc-SUMO2, HDAC3

In another embodiment of the method of the invention, when detection is effected by a the two-hybrid screen, any system known in the art may be used, including, but not limited to, yeast system (e.g. GAL4-VP16) or the mammalian two-hybrid system.

In another embodiment, when detection is effected using indirect screening assays, binding of the compound can be detected indirectly upon SUMOylation of the nuclear receptor protein. The detection may be carried out on protein, DNA or RNA levels. SUMOylation may be detected indirectly via binding of the SUMOylated nuclear receptor protein to a co-repressor bound to DNA. For these binding interactions, any technique for protein-protein interactions known in the art may be used, as described above.

The binding of the SUMOylated nuclear receptor protein to its co-repressor can lead to an alteration of the resulting complex interaction with DNA. This interaction may be assayed by the chromatin immunoprecipitation technique, amongst others.

Further examples of indirect detection of SUMOylation include, but are not limited to, the detection of products of reporter genes (example of reporter genes include but are not limited to luciferase, β-galactocidase, green fluorescent protein), the products of endogenous genes, e.g. the transcribed DNA product, i.e. RNA, or the translated protein. The detection of RNA may be carried out by any technique for RNA detection known in the art, for example, Northern blotting. The translated protein product may be detected by any technique for protein detection known in the art, for example, Western blotting or any other antibody using techniques.

The screening methods may be performed in vitro or in vivo, dependent on the required assay conditions.

The present invention provides methods of screening for compounds that regulate SUMOylation of a nuclear receptor protein comprising contacting the compound of interest with the nuclear receptor protein and detecting SUMOylation of the nuclear receptor protein.

In one embodiment, the compound binds to the nuclear receptor protein and activates SUMOylation of the nuclear receptor protein. Detection of SUMOylation may be carried out using direct and/or indirect screening assay, including but not limited to the screening assays discussed above.

In another embodiment, SUMOylation is detected using co-immunoprecipitation.

Examples of nuclear receptor proteins include but are not limited to PPARα, PPARβ (also known as PPARδ), PPARγ, LXRα, LXRβ, FXR or RXRα, ERα, ERβ, GR, MR, PR, AR, VDR, RXRα, RXRβ, RXRγ, RARα, RARβ, RARγ, TRα, TRβ, PXR, SF-1, LRH1, SHP, TLX, PNR, Nurr1, Nur77, Nor1, RORα, RORβ, RORγ, ERRα, ERRβ, ERRγ, TR2, TR4, GCNF, HNF-4, COUP-I and COUP-II. or the like.

Compounds that bind nuclear receptor proteins and regulate SUMOylation include, but are not limited to, small molecules, peptides, proteins, antibodies and derivatives and fragments thereof, drugs and/or combinations thereof.

The present invention also provides methods of screening for a compound that regulates inflammation by activating SUMOylation of nuclear receptor proteins associated with inflammation comprising contacting the compound of interest with the nuclear receptor protein and detecting SUMOylation of the nuclear receptor protein. Detection of SUMOylation may be carried about by, for example, methods described above.

In one embodiment, regulation of inflammation may be effected by contacting a compound of interest to a nuclear receptor protein and activating SUMOylation of the nuclear receptor protein, thereby inhibiting inflammation. SUMOylation may be detected using, for example, direct and indirect methods described above.

The invention provides a method of screening for a compound that regulates SUMOylation of the peroxisome proliferator-activated receptor (PPAR) comprising contacting a compound of interest to the peroxisome proliferator-activated receptor and detecting SUMOylation of peroxisome proliferator-activated receptor, thereby screening for a compound that regulates SUMOylation.

Examples of peroxisome proliferator-activated receptor proteins include, but are not limited to, PPARα, PPARδ, PPARγ.

In one embodiment, SUMOylation of PPAR, is effected by contacting a compound of interest with PPAR, thereby activating SUMOylation of PPAR. SUMOylation of PPAR may be detected using direct and indirect screening methods, including but not limited to the screening methods described above.

The invention provides a method for repressing inflammation comprising contacting a compound of interest with a nuclear receptor protein so as to activate SUMOylation of the nuclear receptor protein and thereby repressing inflammation.

In one embodiment, the compound that represses inflammation is a small molecule. In another embodiment, the compound that represses inflammation is a protein (including portions or derivatives thereof) and/or peptide. In a further embodiment, the compound that represses inflammation is a combination of a peptide and a small molecule.

In another embodiment, inflammation may be repressed or inhibited by contacting the compound of interest with a nuclear receptor protein, thereby activating SUMOylation of the nuclear receptor protein and repressing expression of an inflammatory gene, thereby repressing inflammation.

In one embodiment, the invention provides methods for repressing transcriptional activation of inflammatory response genes in cells (e.g., macrophages) by SUMOylating a peroxisome proliferator-activated receptor γ (PPARγ). This mechanistic pathway can involve ligand-dependent SUMOylation of a specific lysine residue within the, e.g., PPARγ ligand-binding domain, which targets PPARγ to NCoR/HDAC3 corepressor complexes on inflammatory gene promoters. This inhibits and/or prevents recruitment of the ubiquitylation/19S proteosome machinery that normally mediates signal-dependent removal of corepressor complexes required for gene activation. An analogous mechanism is used by the orphan nuclear receptor Tailless to repress inflammatory gene expression in *Drosophila* cells, revealing an evolutionarily conserved strategy for transrepression of genes that control homeostasis and immune responses.

In accordance with the invention, the method provides sequential steps of a regulated pathway that mediates PPARγ transrepression of inflammatory gene expression by preventing the signal-dependent dismissal of NCoR required for gene activation.

The invention provides methods for determining whether a compound on interest represses activation of inflammatory genes. The method comprises (a) transfecting a cell with (i) a plasmid expressing a nuclear receptor protein, (ii) SUMO ligase siRNA or control siRNA, and (iii) a reporter gene. The method further comprises (b) contacting the transfected cell with the compound. Additionally, the method comprises assaying for compound dependent SUMOylation of the nuclear receptor protein by detecting transcriptional activation of a reporter gene. In one embodiment, the activation of the reporter gene in the presence of SUMO-ligase siRNA, but not in the presence of control siRNA, being indicative that the compound represses activation of inflammatory genes.

An example of a plasmid expressing a nuclear receptor protein includes but is not limited to a plasmid expressing PPARγ. An example of a SUMO-ligase siRNA includes, but is not limited to, Ubc9-siRNA. An example of a reporter gene includes but is not limited to iNOS-luciferase.

In one embodiment, the method for determining whether a compound represses activation of inflammatory genes may include a transient transfection assay. Herein, cells are transfected with (i) a plasmid expressing PPARγ, (ii) UBC9-siRNA or control siRNA and (iii) an iNOS-luciferase reporter. The nuclear receptor protein ligand (for example, rosiglitazone (Ro)), is tested for its ability to repress transcriptional activation of an inflammatory gene promoter, (for example iNOS), fused to a reporter gene, (for example luciferase), in the presence or absence of an siRNA directed against the SUMO ligase, (for example SUMO E2 ligase).

In an embodiment, repression of inflammatory gene activation in the presence of control siRNA and reversal of this repression by the SUMO ligase siRNA provides a highly specific signature of SUMOylation-dependent repression that is scalable to a high throughput screen.

The invention provides methods for determining whether a compound of interest represses activation of inflammatory genes comprising contacting a cell expressing both, a co-repressor protein joined to first label and nuclear receptor protein joined to second label, with the compound of interest, and then assaying for the interaction of nuclear repressor protein and co-repressor protein with each other. Interaction may be determined by detecting transcriptional activation of a reporter gene (e.g. having GAL4 binding sites). The activation of the reporter gene may be indicative that the compound represses activation of inflammatory genes.

In one embodiment, the first and second labels can be different and the co-repressor protein joined to a first label includes, but is not limited to, NcoR joined to the DNA binding domain of GAL4 and a nuclear receptor protein joined to a second label includes, but is not limited to, PPARγ joined to VP16.

Merely by way of example, another approach for high throughput screening involves a mammalian two-hybrid assay which can be used to indirectly measure SUMOylation. In one embodiment of this assay, the fragment of a corepressor protein, (for example NcoR or HDAC3), that interacts with SUMOylated nuclear receptor protein, (for example PPARγ), is fused to the DNA binding domain of GAL4, to form a GAL4-co-repressor fusion protein. The VP16 transactivation domain can be fused to the nuclear receptor protein, to form a VP16-nuclear receptor fusion protein. When compounds stimulate SUMOylation of the nuclear receptor protein, the VP-16 nuclear receptor fusion protein interacts with the GAL4-co-repressor fusion protein. This would result in transcriptional activation of a reporter gene containing GAL4 binding sites.

The method for determining whether a compound causes the nuclear receptor protein to interact with the corepressor protein comprises separately contacting each of a plurality of samples to be tested according to any of the methods of the invention. In one embodiment, the plurality of samples may comprise, more than about $10^4$ or more than about $5 \times 10^4$ samples. In another particular embodiment, the method comprises essentially simultaneously screening the molecules according to any one of the described methods of the invention.

The invention also provides methods for inhibiting an immune response by SUMOylating a nuclear receptor protein. One embodiment of the invention comprises contacting nuclear receptor protein positive cells with a compound that binds and activates SUMOylation of the nuclear receptor protein, thereby inhibiting the immune response.

The invention further provides methods for inhibiting and/or treating an immune system disease is by inhibiting an inflammatory response by contacting a nuclear receptor protein with a compound that activates SUMOylation of nuclear receptor protein and represses expression of inflammatory genes. Examples of suitable compounds include Rosiglitazone (Ro).

The invention further provides methods of inhibiting an inflammatory response by SUMOylating a nuclear receptor protein. In one embodiment, the method comprises contacting nuclear receptor protein positive cells with a compound that binds and activates SUMOylation of a nuclear receptor protein, thereby inhibiting an inflammatory response.

In one embodiment, the inflammatory response inhibited is Type II diabetes. In another embodiment, the inflammatory response inhibited is atherosclerosis.

The present invention also provides methods for inhibiting expression of inflammatory genes comprising contacting nuclear receptor protein positive cells with a compound that binds and activates SUMOylation of the nuclear receptor protein, thereby inhibiting expression of inflammatory genes.

In one embodiment, expression of inflammatory genes is inhibited by a compound of interest that binds and activates SUMOylation of the nuclear receptor protein and represses inflammatory genes.

In one embodiment, a nuclear receptor protein that inhibits an immune response and/or inhibits an inflammatory response and/or inhibits expression of inflammatory genes is PPARγ.

In another embodiment, a nuclear receptor protein that inhibits an immune response and/or inhibits an inflammatory response and/or inhibits expression of inflammatory genes is PPARα.

In yet another embodiment, a nuclear receptor protein that inhibits an immune response and/or inhibits an inflammatory response and/or inhibits expression of inflammatory genes is PPARδ.

In a further embodiment, a nuclear receptor protein that inhibits an immune response and/or inhibits an inflammatory response and/or inhibits expression of inflammatory genes is LXRα.

In an additional embodiment, a nuclear receptor protein that inhibits an immune response and/or inhibits an inflammatory response and/or inhibits expression of inflammatory genes is LXRβ.

The invention also provides uses of a nuclear receptor protein for inhibiting an immune response by SUMOylating a nuclear receptor protein, comprising contacting the nuclear receptor protein positive cells with a compound that binds and activates SUMOylation of a nuclear receptor protein, thereby inhibiting an immune response.

The invention further provides uses of a nuclear receptor protein for inhibiting an inflammatory response by SUMOylating a nuclear receptor protein, comprising contacting the nuclear receptor protein positive cells with a compound that binds and activates SUMOylation of a nuclear receptor protein, thereby inhibiting an inflammatory response.

The present invention also provides uses of a nuclear receptor protein for inhibiting expression of inflammatory genes by SUMOylating a nuclear receptor protein, comprising contacting the nuclear receptor protein positive cells with a compound that binds and activates SUMOylation of the nuclear receptor protein, thereby inhibiting expression of inflammatory genes. The binding of a compound to the nuclear receptor protein activates SUMOylation of the nuclear receptor protein and may repress inflammatory genes.

The invention further provides compounds identified by the methods of the invention.

The compounds obtained by screening methods of the claimed invention may be administered as a sole active ingredient or in combination with other anti-inflammatory agents, such as NSAID's or other anti-inflammatory drugs. Where the compounds obtained by screening methods of the invention are administered in conjunction with other anti-inflammatory agents, e.g. as hereinabove specified, dosages of the co-administered anti-inflammatory compound will of course vary depending on the type of co-drug employed, on the specific drug employed, on the condition being treated and so forth.

Further the present invention contemplates therapeutic combinations, e.g. a kit, comprising compounds obtained by screening methods of the claimed invention, in free form or in pharmaceutically acceptable salt form, to be used concomitantly or in sequence with at least one pharmaceutical composition comprising an immunosuppressant, immunomodulatory or anti-inflammatory drug e.g., a DMARD, NSAID, glucocorticoid or corticosteroid. The kit may comprise instructions for its administration. The kits of the invention can be used in any method of the present invention.

The following examples are presented to illustrate the present invention and to assist one of ordinary skill in making and using the same. The examples are not intended in any way to otherwise limit the scope of the invention.

Example 1

This example details the molecular mechanism by which PPARγ represses transcriptional activation of inflammatory genes.

Methods

Plasmids and Cell Culture

Primary macrophages were elicited by intra-peritoneal injection with 2 ml of thioglycollate. *Drosophila* SN2 cells were cultured in Schneider media with 10% serum. HA-tagged PPARγ WT and mutants at K77R and K365R were cloned into the pcDNA3 backbone (Invitrogen). WT-PIAS1 and PIAS1-N were cloned into a 2×FLAG-pcDNA3 expression vector. PPARγ bait used for yeast two-hybrid including the DNA-binding domain, hinge region and ligand binding domain (PPARγ DHL) was inserted into the pGBK7 vector (Clontech). *Drosophila* tailless was cloned into pACv.5 vector (Invitrogen). dsRNAs were generated by PCR and in vitro transcription through T7 promoter sequences adapted to PCR ends. For RNAi experiments, smart-pool siRNAs (Dharmacon) against PIAS1, Ubc9, HDAC3, HDAC7 or control non-specific and previously validated NCoR were transfected using lipofectamine 2000 (Invitrogen) into primary macrophages and incubated for 48 h. Effects of these siRNAs on cellular protein levels are illustrated in Figure S1.

Yeast Two Hybrid Screen

Yeast two-hybrid library was generated in the pGAD vector (Clontech) with RNA derived from primary peritoneal macrophages elicited from normal and hypercholesterolemic mice. The library was transformed into the AH109 yeast strain and was mated to Y187 strain transformed with PPARγ DHL bait. Colonies were picked 4-6 d post mating. PCR inserts were amplified and sequenced. Yeast plasmids were purified from individual clones. Finally, interactions were verified by α-galactosidase activity in yeast liquid culture assays.

Transient Transfection

The RAW264.7 mouse macrophage cell line was transiently transfected with plasmids containing the iNOS or Aox-TK promoters directing luciferase expression as previously described 22. For transrepression experiments, wild-type PPARγ or PPARγ mutants were transfected at a 3:1 ratio to reporter plasmids using Superfect reagent (Qiagen). For siRNA experiments, RAW264.7 cells were transfected with siRNAs (40 nM) using Superfect reagent for 48 h prior to activation with PPARγ ligands and LPS induction. In all transfections, cells were treated with 1 μM rosiglitazone (Ro) and stimulated with 1 μg/ml LPS and luciferase activity assayed 6 h later. Transfection experiments evaluated each experimental condition in triplicate and results were expressed as mean +/− standard deviation. Each transfection experiment was independently repeated at least three times. Statistical analysis was preformed using Student's t-test with $P<0.01$ considered statistically significant.

Chromatin Immunoprecipitation Assays $2-4 \times 10^6$ primary macrophages or RAW 264.7 cells were used per experimental point. Cells were pre-treated with 1 μM Ro (1 h) and stimulated with 1 μg/ml LPS (1 h). Cross-linking was carried out for 10 min with 1% formaldehyde and cells lysed with 1% SDS, 10 mM EDTA, 50 mM Tris-HCl pH 8.1 and sonicated 10 sec-5 times. Five μg antibody conjugated to sheep anti-rabbit dyna-beads (Dyna1) were used for immunoprecipitations. For PPARγ, 2 μg of H-100 plus 3 μg of PPARγ antibody from Geneka were used in combination. Alternatively, anti-HA protein A sepharose beads (Covance) were used for wild-type and mutant HA-tagged PPARγ proteins. HDAC3 and p65 antibodies were from SantaCruz. NCoR antibody was from Affinity Bioreagents, Inc. Beads were washed twice with wash buffer: 150 mM NaCl, 0.1% SDS, 1% Triton X-100, 2 mM EDTA, 20 mM Tris-HCl and subsequently with buffer: 0.25 M LiCl, 1% NP-40, 1% deoxycholate, 1 mM EDTA, 10 mM Tris-HCl. Beads were eluted in 300 μl of TE with 1% SDS and 0.1 M $NaCO_3$. Elute samples and 10% inputs were reversed at 65° C. for a minimum of 6 h. DNA was purified by phenol-chloroform and ethanol precipitation and 10 ng of total DNA was used for each PCR reactions.

RNA Isolation, Semi-Quantitative PCR and Northern Blot Analysis

Total RNA (Trizol method) was prepared from thioglycollate-elicited primary macrophages pre-treated with 1 μM Ro (2 h) prior to 1 μg/ml LPS stimulation (6 h). One μg of total RNA was used for cDNA synthesis using the First-strand synthesis RT system (Invitrogen). Two μl of cDNA was used for PCR using iNOS or inflammatory gene specific primers amplifying a 0.7 kb region of cDNA. GAPDH cDNA samples were carried out for 22 to 25 cycles. For Northern blot analysis, 10 μg of total RNA and an iNOS-specific probe were utilized.

Co-Immunoprecipitations and Western Blotting

For co-immunoprecipitations, RAW264.7 cells or 293 cells were transfected using Superfect reagent according to manufacturer's protocol with HA-PPARγ WT and 2×FLAG-PIAS1 WT in 10 cm dishes. Whole cell extracts (WCEs) were prepared using WCE lysis buffer: 10 mM Tris-HCl pH 8, 420 mM NaCl, 1 mM EDTA and 0.5% NP-40 with protease inhibitor cocktail (Roche Bochem.). 250 μg of total protein were immunoprecipitated using anti-HA agarose beads (Covance). Immunoprecipitates were washed 4 times with Wash Buffer containing 10 mM Tris-HCl pH8, 100 mM NaCl, 1 mM EDTA, 0.5% NP-40 and 0.5% Triton X-100 followed by boiling in 1× sample loading buffer and 10% SDS-PAGE. M2 anti-flag antibody was used at 1:1000 dilution (Sigma). HA immunoblotting was carried out at 1:1000 dilution (Covance).

SUMOylation Assays

For in vivo SUMOylation experiments, 250 μg of total protein extracts were prepared form HeLa cells transfected with HA-tagged PAPRγ WT or SUMO point mutants: K77R and K365R, and Myc-tagged SUMO-1. Cell lysates were immunoprecipitated for HA-tagged PPARγ and subsequently washed 4 times in wash buffer containing 0.5% TritonX-100, 0.1% SDS, 1 mM EDTA, 20 mM Tris-HCl pH 7.8 and 500 mM NaCl. Immunoprecipitates were resolved on 10% SDS PAGE gels, transferred to nitrocellulose membranes and blotted for anti-HA or anti-Myc.

Experimental Details of FIGS. 1, 2, 3b-g, 4, 5b-g, 7, 8, 9c and 15.

In FIG. 1a, primary macrophages were transfected with NCoR siRNA or control (lamin) siRNA for 48 h prior to pre-treatment with 1 μM rosiglitazone (Ro) or GW0072 and stimulated with LPS for 6 h. Total RNA was analyzed for iNOS and GAPDH mRNA by Northern Blotting. In FIG. 1b, RAW264.7 cells were transfected with the indicated siRNAs and PPARγ expression and iNOS-luciferase reporter plasmids. Cells were treated with LPS and/or Ro as in panel a prior to assay of luciferase activity. In FIG. 1c, primary macrophages were pre-treated with 10 nM Trichostatin A (TSA) for 1 h followed by treatment with 1 μM Ro for 2 h. Cells were stimulated with LPS for 6 h and total RNA was analyzed as in FIG. 1a. In FIG. 1d, RAW264.7 cells were transfected with the indicated siRNAs and PPARγ expression and iNOS-luciferase reporter plasmids. Cells were treated with LPS and/or Ro as in FIG. 1a, prior to assay of luciferase activity. In FIG. 1e, primary macrophages were pretreated with Ro or GW0072 for 1 h followed by 1 h LPS induction and formaldehyde crosslinking. A 150 base pair region of the iNOS promoter spanning the most proximal NF-κB site to the start of transcription was analyzed by ChIP assays using the indicated antibodies. In FIG. 1f, RAW264.7 cells were transfected with the indicated siRNAs and PPARγ expression and iNOS-luciferase reporter plasmids and stimulated with LPS for 6 h prior to assay of luciferase activity. Error bars in this and succeeding figures represent standard deviations triplicate, independent determinations. * indicates p<0. compared to Ro repression; ** refers to p<0.01 compared to LPS induction.

In FIG. 2a, CHIP analysis of NCoR and Ubc5 occupancy on the iNOS promoter was performed in primary macrophages stimulated with LPS for the indicated times in the presence or absence of Ro. In FIG. 2b, Semi-quantitative RT-PCR analysis of iNOS and GAPDH mRNA in primary macrophages. Cells were treated with Ro 1 h before (pre) or 1 h following (post) stimulation with LPS. RNA was isolated for analysis 6 h after LPS treatment. In FIG. 2c, ChIP analysis for p65 and PPARγ on iNOS and CD36 promoters in primary macrophages was performed as described in FIG. 2a. In FIG. 2d, ChIP analysis of the iNOS promoter for NCoR and PPARγ was carried out in primary macrophages 1 h following LPS stimulation. Ro was given 1 h before (pre) or 1 h after (post) stimulation. Cells were transfected with control or NCoR-specific siRNAs 48 h prior to LPS stimulation. In FIG. 2e, Expression data derived from microarray analysis of primary macrophages treated with LPS in the presence or absence of the PPARγ-specific agonist GW7845. In FIG. 2f, ChIP analysis for NCoR and PPARγ on the indicated promoters was carried out using primary macrophages as in 2d.

Figure 3:
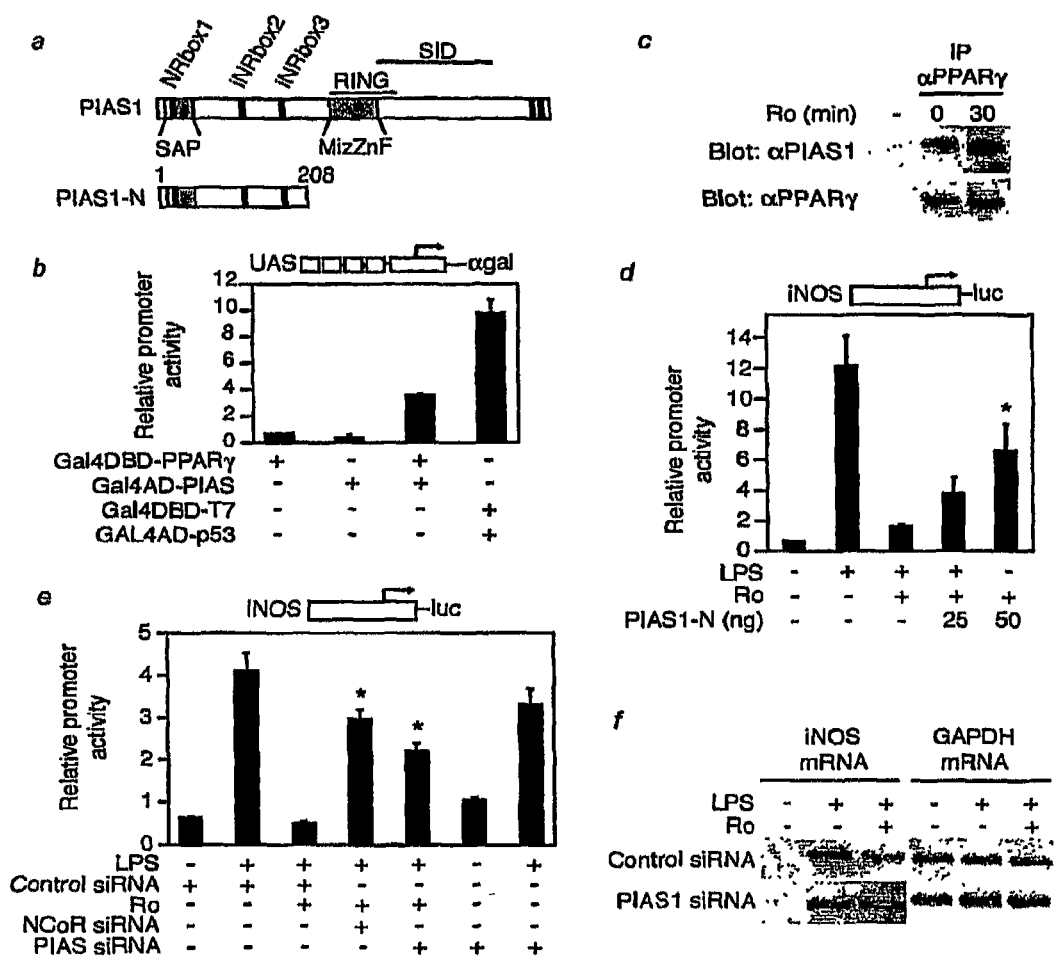
FIG. 3. 3a shows the schematic diagram of WT-PIAS1 and PIAS1-N isolated from a yeast two-hybrid screen. NRbox1, 2,3, motifs mediating nuclear receptor interaction; SAP, scaffold attachment protein, first identified as chromatin interaction domain; RING, domain essential for E3 ligase activity. Yeast two hybrid analysis (3b), Western blot analysis (3c and 3g), luciferase gene activity (3d and 3e) and semi-quantitative RT-PCR (3f) show that PIAS1 interacts with PPARγ and is required for ligand-dependent inhibition of iNOS gene activation.
Figure 4:
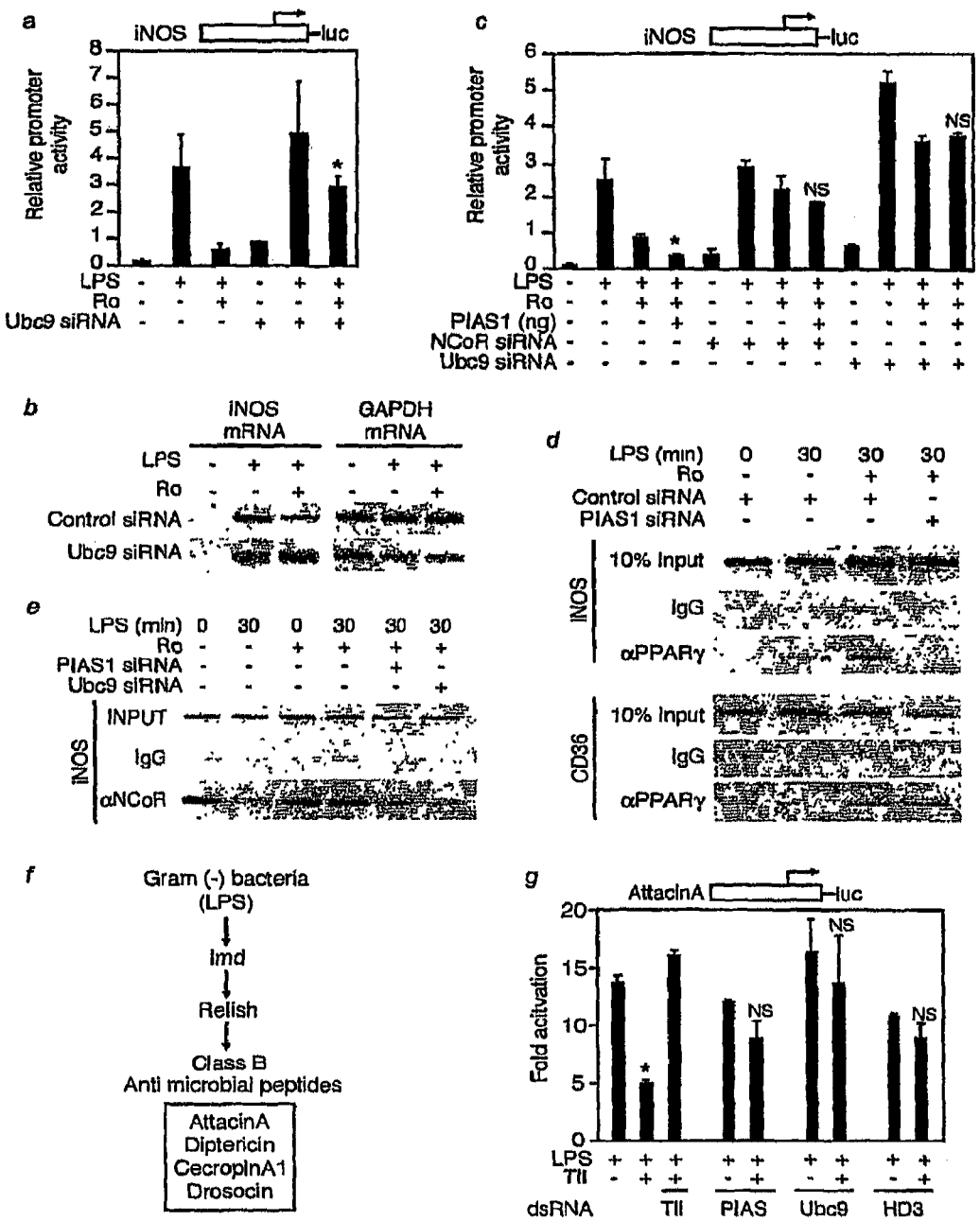
FIG. 4. Luciferase gene activity (4a, 4c and 4g), semi-quantitative RT-PCR (4b), chromatin immunoprecipitation (4d and 4e) show that PIAS1-dependent SUMOylation is required for transrepression by PPARγ and the Drosophila orphan receptor tailless (tll). 4f shows the LPS signaling pathway responsible for transcriptional activation of the Attacin A promoter in Drosophila melanogaster.

In FIG. 3b, yeast two-hybrid assay assessing interactions between PPARγ and PIAS1. Gal4 DBD-T7 and Gal4AD-p53 serve as a positive control. In FIG. 3c, primary peritoneal macrophages were treated with Ro for 0 or 30 min as indicated. Whole cell extracts were immunoprecipitated for PPARγ and the immunoprecipitates were subsequently subjected to western blot analysis using either anti-PPARγ or anti-PIAS1 antibodies. In FIG. 3d, RAW264.7 cells were co-transfected with the iNOS-luciferase reporter, PPARγ and PIAS1-N expression plasmids as indicated. 36 h post-transfection, cells were treated with Ro and LPS for 6 h prior to assay of luciferase activity. In FIG. 3e, RAW264.7 cells were transfected with the iNOS reporter, PPARγ expression plasmid and the indicated siRNAs. Cells were treated with Ro and LPS 36 h post-transfection and assayed for luciferase activity 6 h later. * indicates p<0.001 compared to Ro repression. In FIG. 3f, primary macrophages were transfected with control siRNA or PIAS1-specific siRNA as indicated. Cells were pre-treated with Ro for 2 h followed by 6 h LPS stimulation. Expression of GAPDH and iNOS endogenous genes was analyzed by semi-quantitative RT-PCR. In FIG. 3g, Immunoblots (B) for FLAG (FL)-tagged PIAS1 and HA-tagged PPARγ in transfected RAW264.7 macrophages (left panel of FIG. 3g) or endogenous PIAS1 and PPARγ in primary macrophages (right panel of FIG. 3g).

In FIG. 4a, RAW264.7 cells were transfected with the iNOS reporter, PPARγ expression plasmid and Ubc9-siRNA. 36 h post-transfection cells were pretreated with Ro for 1 h and LPS for 6 h prior to assay of luciferase activity. In FIG. 4b, primary macrophages were transfected with control or Ubc9 siRNAs, treated with LPS and Ro as indicated and RNA isolated for semi-quantitative RT-PCR 6 h later. In FIG. 4c, RAW264.7 cells were transfected with the indicated siRNAs, PIAS1 and PPARγ expression vectors, and the iNOS-luciferase reporter gene. Cells were pretreated with Ro for 1 h and LPS for 6 h prior to assay of luciferase activity. In FIG. 4d, ChIP experiments were carried out in primary macrophages transfected with control or PIAS1 siRNAs for 48 h prior to pre-treatment with 1 μM ligand followed by 0 or 30 min stimulation with LPS. In FIG. 4e, ChIP analysis of NCoR on the iNOS promoter was carried out in primary macrophages pre-treated with ligand followed by LPS stimulation. Macrophages were transfected with siRNA against PIAS1 or Ubc9 as indicated. In FIG. 4f, LPS signaling pathway responsible for transcriptional activation of the Attacin A promoter in *Drosophila melanogaster* is shown. In FIG. 4g, Schneider cells (SN2) were transiently transfected with Attacin A luciferase reporter and tll expression plasmid in the presence of the indicated dsRNAs for 48 h followed by LPS treatment (6 h) and assay of luciferase activity. * indicates p<0.001 compared to Ro or tll repression; NS is non-significant.

Figure 5:
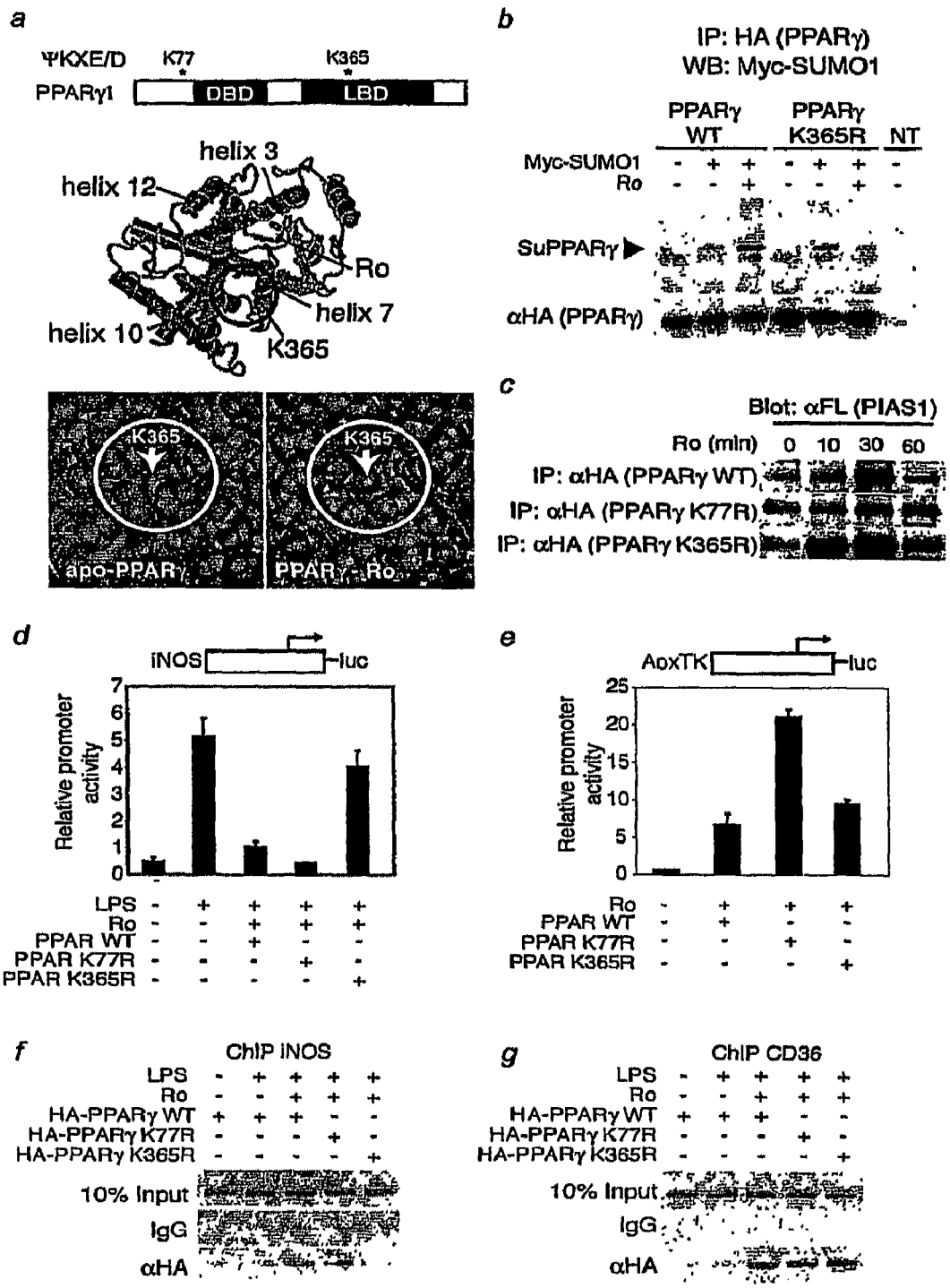
FIG. 5. In 5a, the upper panel shows a schematic representation of full-length PPARγ with two consensus SUMOylation sites at K77 and K365. The panel below illustrates the overall fold of the PPARγ ligand binding domain, indicating the location of K365 in helix 7. The lower left panel illustrates a close-up of this region of the apo PPARγ LBD surface, with the arrow pointing to a hydrogen atom in the K365 side chain. Lower right panel illustrates the same region of the PPARγ LBD bound to Ro. The arrow indicates the nitrogen atom of the primary amine of K365 that is solvent-exposed. Immunoprecipitation followed by Western blot analysis (5b and 5c), luciferase gene activity (5d and 5e) and chromatin immunoprecipitation (5f and 5g) show that ligand-dependent SUMOylation of PPARγ K365 is required for transrepression.

In FIG. 5b, in vivo detection of SUMOylation of PPARγ was performed in HeLa cells transfected with myc-tagged Sumo1 and HA-tagged WT-PPARγ or PPARγ$^{K365R}$. Cells were immunoprecipitated for HA tag and blotted for myc tag. NT refers to non-transfected cells. In FIG. 5c, RAW264.7 cells were transfected with wild-type (WT) and mutant HA-PPARγ and Flag(FL)-tagged PIAS1 expression plasmids and treated with Ro for 0, 10, 30 or 60 min. Whole cell extracts were immunoprecipitated for HA tag followed by western blotting for FL-PIAS1. In FIG. 5d, RAW264.7 cells were transfected with the iNOS reporter gene and expression plasmids for WT or mutant forms of PPARγ. Cells were treated 48 h post-transfection with ligand and stimulated with LPS (6 h). In FIG. 5e, transactivation assays were performed in RAW264.7 cells transfected with the AOx-Tk luciferase reporter gene[22] and expression plasmids for the indicated wild-type and mutant forms of PPARγ. In FIG. 5f, ChIP analysis for HA-tagged wild-type and mutant forms of PPARγ on the iNOS promoter was performed in RAW264.7 cells treated with Ro and LPS. In FIG. 5g, WT and mutant forms of PPARγ are recruited to the CD36 promoter. ChIP analysis for HA-tagged PPARγ was performed on the CD36 promoter as in 5f.

Figure 7:
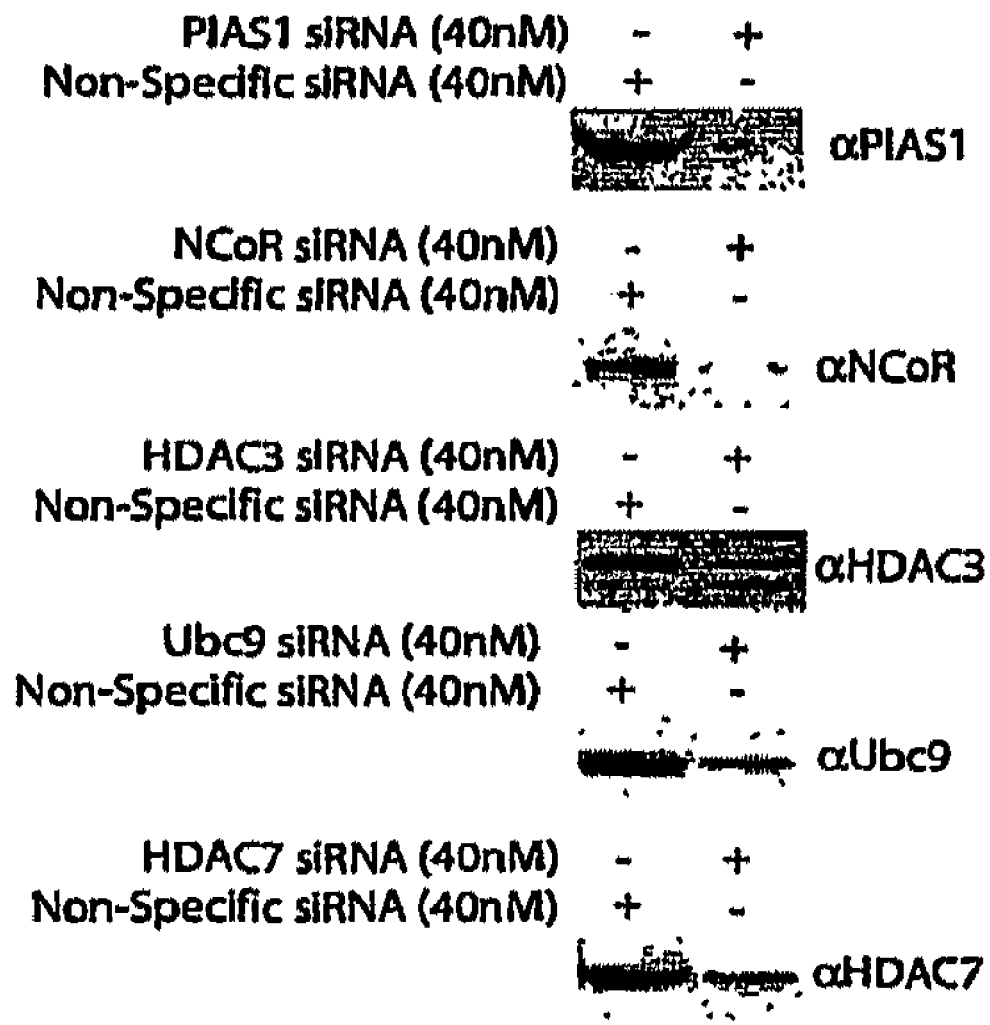
FIG. 7. Efficacy of siRNAs directed against NCoR, HDAC3, HDAC7, PIAS1 and Ubc9.
Figure 8:
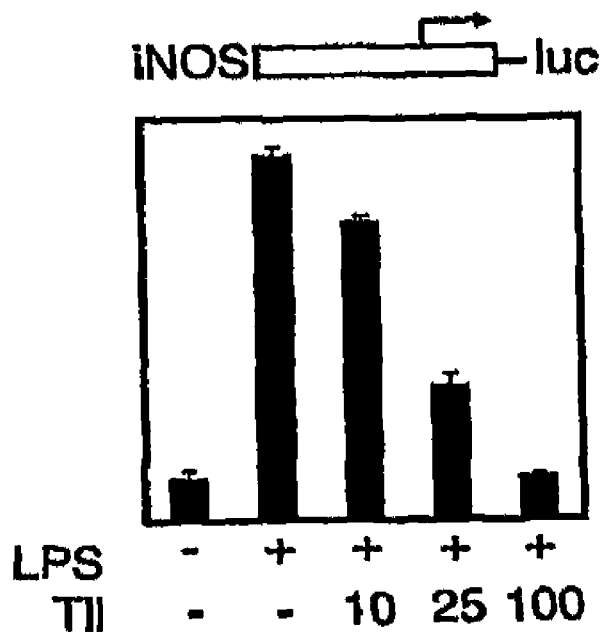
FIG. 8. Luciferase gene activity (8a) and T11 SUMOylated species separated by SDS-PAGE and visualized by autoradiography showed that tailless is SUMOylated in vitro and represses iNOS induction by LPS in RAW264.7 cells.
Figure 8:
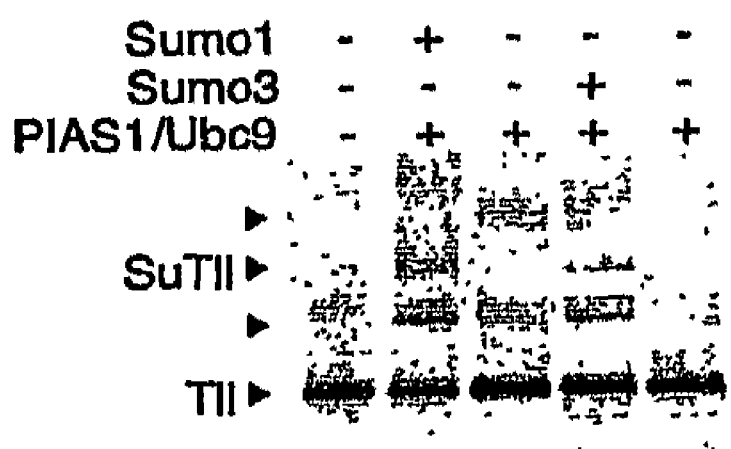

In FIG. 7, primary macrophages were transfected with the indicated specific and control siRNAs. Whole cell extracts were prepared 48 hours later and assayed for the indicated proteins by Western Blotting.

In FIG. 8a, Tailless was expressed in RAW264.7 cells using 10, 25, and 100 ng of expression plasmid and 100 ng of iNOS reporter. Cells were treated with LPS 48 h post-transfection (6 h). In FIG. 8b, Tailless was in-vitro translated from a T7 promoter and radiolabelled with S$^{35}$ Met. Iii-vitro SUMOylation assays were carried out according to manufactures' protocol (LAE Biotech.). Tll SUMOylated species were separated by SDS-PAGE and visualized by autoradiography.

In FIG. 9c, Macrophages were transfected with mammalian two-hybrid reporter, VP-16 PPARγWT and either GalDBD-HDAC3 or GalDBD. Control or Ubc9 siRNA was co-transfected and cells were cultured with 0.01 μM TSA prior to treatment with 1 μM Ro. Cells were assayed for luciferase activity 16 hours after Ro treatment.

Figure 15:
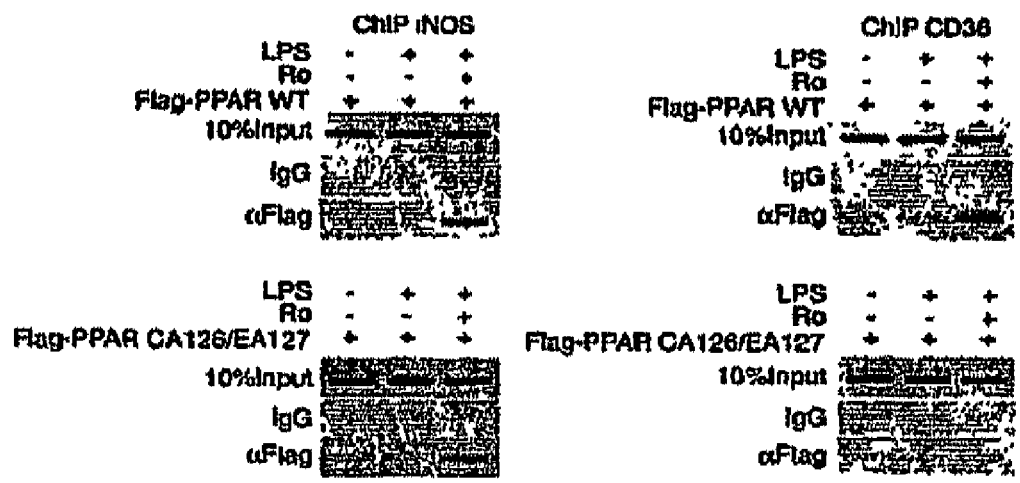
FIG. 15. Trans repression does not require sequence specific DNA binding.

In FIG. 15, RAW264.7 cells were transfected with flag-tagged wild type PPARγ or flag-tagged PPARγ$^{CA126/EA127}$. Ligand-dependent recruitment of tagged PPARγ proteins to the endogenous iNOS and CD36 promoter was determined by ChIP assay using anti-Flag antibody.

The NCoR/HDAC3/TBL Complex is a Target of PPARγ-Mediated Transrepression

We initially focused on the inducible nitric oxide synthase (iNOS) gene as a model because it is one of several inflammatory response genes expressed by macrophages that are linked to the pathogenesis of atherosclerosis and insulin resistance[39,40]. The iNOS gene is strongly induced in macrophages by lipopolysaccharide (LPS)[41] and is negatively regulated by PPARγ agonists in a PPARγ-dependent manner[22]. Inhibition of NCoR expression using an NCoR-specific siRNA validated for efficacy[36] (and FIG. 7) resulted in a complete reversal of iNOS transrepression by rosiglitazone but not by a control siRNA (FIG. 1a). Intriguingly, similar results were obtained utilizing a selective PPARγ modulator (GW0072) that is effective at dissociating NCoR from PPARγ, but only weakly stimulates interactions with nuclear receptor coactivators[42] (FIG. 1a). Consistent with these findings, knockdown of NCoR expression, but not SMRT expression, resulted in a reversal of repression of an iNOS promoter reporter by liganded PPARγ in RAW264.7 macrophages (FIG. 1b). Potential roles of NCoR-associated HDACs were supported by the finding that treatment with as little as 10 nM of the histone deacetylase inhibitor, Trichostatin A, reversed rosiglitazone-dependent transrepression of iNOS (FIG. 1c). To specifically evaluate the role of HDAC3, which is an essential component of NCoR/HDAC3/TBL corepressor complexes[32,35], the effect of an HDAC3-specific pool of siRNAs was tested in RAW264.7 cells. The validated HDAC3-specific siRNAs, but not a control siRNA directed against HDAC7, completely reversed the transrepression observed on the iNOS promoter in this assay system (FIG. 1d).

The observation that transrepression of the iNOS gene by rosiglitazone required NCoR and HDAC3 predicted that NCoR/HDAC3/TBL complexes should associate with the iNOS promoter. Chromatin immunoprecipitation (ChIP) experiments confirmed that NCoR, HDAC3, TBL1 and TBLR1 were present on the iNOS promoter under basal conditions and that the NCoR and HDAC3 components of this complex were cleared following LPS stimulation (FIG. 1e). However in cells treated with rosiglitazone or GW0072, both NCoR and HDAC3 remained on the iNOS promoter after LPS stimulation (FIG. 1e). Because signal-dependent induction of NF-κB target genes has been suggested to require removal of NCoR complexes through Ubc5-dependent ubiquitylation[36], we evaluated the importance of these events for activation of the iNOS promoter by LPS. As shown in FIG. 1f, validated siRNAs directed against TBL1, TBLR1 and the ubiquitin conjugating enzyme Ubc5c[35], but not a control siRNA, inhibited iNOS induction in response to LPS. These data are consistent with the hypothesis that the TBL1/TBLR1-recruited ubiquitylation complex is required for LPS-dependent clearance of NCoR and HDAC3 from the iNOS promoter as a prerequisite to transcriptional activation, and that PPARγ acts to repress iNOS activation by preventing this TBL1/TBLR1-dependent corepressor clearance.

We next evaluated whether an ordered sequence of events was required for NCoR clearance in response to LPS stimulation in the presence or absence of rosiglitazone by ChIP assay. While NCoR was cleared from the iNOS promoter within 10 minutes of LPS induction, pretreatment of cells with rosiglitazone inhibited clearance at all time-points tested (FIG. 2a). Significantly, Ubc5 was rapidly recruited to the iNOS promoter following LPS stimulation in the absence of rosiglitazone, but was not recruited to the promoter in its presence (FIG. 2a). These results suggest that PPARγ acts to repress LPS induction of the iNOS gene by preventing recruitment of the Ubc5/19S proteosome machinery required for the clearance of NCoR and HDAC3. Consistent with this, rosiglitazone was unable to inhibit the induction of iNOS expression if added to cells following addition of LPS (FIG. 2b), suggesting that once the NCoR complex has been cleared from the promoter, PPARγ is unable to function as a repressor.

These observations raised the question of whether PPARγ is itself recruited to the iNOS promoter, and whether failure of clearance of the NCoR/HDAC3 complex by rosiglitazone influences recruitment of NF-κB factors in response to LPS. ChIP experiments performed in primary macrophages, evaluating both the iNOS promoter and the CD36 promoter, which is positively regulated by PPARγ[43], revealed that PPARγ was recruited to both promoters in a ligand-dependent manner (FIG. 2c). As expected, the p65 component of NF-κB was recruited exclusively to the iNOS promoter in response to LPS, and this recruitment was not affected by rosiglitazone treatment (FIG. 2c). Intriguingly, PPARγ was not recruited to the iNOS promoter if ligand was added after LPS stimulation (FIG. 2d), suggesting a requirement for the NCoR complex. This prediction was confirmed by the finding that ligand-dependent recruitment of PPARγ to the iNOS promoter was abolished by siRNA-mediated knockdown of NCoR (FIG. 2d). In addition, the recruitment of PPARγ to the iNOS promoter did not require sequence specific DNA binding because a point mutation in the DNA binding domain (PPARγ$^{C426/EA127}$) that abolished its ability to bind CD36 promoter did not affect the binding to the iNOS promoter (FIG. 15).

To investigate whether the mechanism by which PPARγ represses induction of iNOS expression is utilized on other PPARγ-sensitive genes, we evaluated additional LPS-inducible promoters that also exhibited increased levels of expression under unstimulated conditions in NCoR-deficient macrophages, including Ccl3, Ccl7, Cxcl10 and Tgtp[37]. The induction of these genes by LPS and repression of the LPS response by the PPARγ agonist GW7845 is illustrated in FIG. 2e. None of these genes contain consensus or near-consensus binding sites for RXR/PPARγ heterodimers within 1 kb of their transcriptional start sites. ChIP analysis confirmed that NCoR was present on each of these promoters under basal conditions and that NCoR was fully or partially dismissed by LPS treatment (FIG. 2f). As in the case of the iNOS promoter, signal-dependent dismissal of NCoR was inhibited by pretreatment of cells with rosiglitazone. Occupancy by PPARγ under basal conditions varied somewhat for each promoter. However, in each case PPARγ binding was enhanced when cells were treated with rosiglitazone prior to stimulation with LPS, but not when cells were stimulated with LPS prior to rosiglitazone treatment (FIG. 2f). Finally, ligand-dependent enhancement of PPARγ occupancy did not occur when NCoR expression was knocked down (FIG. 2f). Although not all PPARγ-sensitive promoters exhibited this pattern, these findings suggest that prevention of NCoR clearance is a broadly used mechanism mediating repressive actions of PPARγ.

PIAS1 Interacts with PPARγ and is Required for Transrepression

The observation that ligand-dependent recruitment of PPARγ to LPS-responsive promoters required NCoR raised a paradox, because the binding of rosiglitazone or GW0072 disrupts direct interactions between NCoR and PPARγ42. To identify PPARγ-interacting proteins that might potentially resolve this paradox, a yeast two-hybrid screen was performed using a library constructed from mRNA derived from primary macrophages. The PPARγ bait vector contained both the DNA and ligand binding domains based on our prior observations that both domains are required for transrepression 28. One of the clones isolated in this screen encoded the initial 208 amino acids of PIAS1 (protein inhibitor of activated STAT1), initially identified as a suppressor of interferon-dependent transcription[44]. PIAS1 belongs to a family of SUMO E3 ligases that contain a central RING domain shown to be important for SUMO ligase activity[45]. The region of PIAS1 isolated in this screen (referred to as PIAS1-N, FIG. 3a) contains motifs previously shown to interact with various nuclear receptors[46-48]. The interaction between PPARγ and the PIAS1 clone was confirmed both by yeast survival and α-Galactosidase liquid assays (FIG. 3b). Furthermore, co-immunoprecipitation experiments using antibodies directed against endogenous PPARγ and PIAS1 demonstrated a basal interaction in primary macrophages that was enhanced by treatment with rosiglitazone (FIGS. 3c and 3g).

SUMOylation of transcription factors has previously been correlated with impaired transcriptional activation and/or transcriptional repression[49-51]. To investigate whether PIAS1 was involved in PPARγ-mediated transrepression, the PIAS1-N fragment identified by yeast two-hybrid screening was initially tested for dominant negative activity in RAW264.7 cells. Overexpression of the PIAS1 N terminus significantly impaired PPARγ-mediated inhibition of the iNOS promoter in a dose-dependent manner (FIG. 3d). Conversely, over-expression of full-length PIAS1 enhanced PPARγ mediated transrepression of the iNOS promoter, also in a dose-dependent manner (FIG. 4c). To confirm this in a loss of function experiment, PIAS1-specific siRNAs were developed that achieved greater than 80% reduction of PIAS1 mRNA and protein in both primary macrophages and RAW264.7 cells (FIG. 7). The PIAS1-specific, but not control, siRNAs resulted in significant inhibition of PPARγ-dependent repression of the iNOS promoter, similar to the effects observed for the NCoR siRNA (FIG. 3e) but did not impair transcriptional activation of a positively regulated PPARγ target gene. Finally, siRNA-mediated knockdown of PIAS1 in primary macrophages abolished PPARγ transrepression of the endogenous iNOS gene (FIG. 3f).

Sumo Ligase Activity is Required for Transrepression by PPARγ and Drosophila Orphan Nuclear Receptors The SUMOylation pathway involves a rate-limiting E2 ligase, Ubc9, which catalyzes the transfer of SUMO groups to target proteins, a reaction that is thought to be stabilized and assisted by E3 ligase family members such as PIAS1[52]. Ultimately, the SUMO group is transferred and conjugated to a molecular target resulting in a specific functional outcome for that substrate[45]. To examine whether these enzymatic activities were required for PPARγ-dependent transrepression, transient transfection assays were performed in RAW264.7 cells using a validated siRNA pool directed against murine Ubc9 (FIG. 7). Knockdown of Ubc9 expression significantly impaired PPARγ-dependent transrepression of the iNOS promoter (FIG. 4a). Similarly, knockdown of Ubc9 expression in primary macrophages resulted in loss of PPARγ-mediated transrepression of the endogenous iNOS gene (FIG. 4b). Correspondingly, when NCoR or Ubc9 expression were knocked down by specific siRNAs, the ability of PIAS1 over-expression to potentiate PPARγ-mediated transrepression was reduced (FIG. 4c). These results suggest that SUMOylation is critical for the function of PIAS1 in PPARγ-dependent transrepression and that PIAS1 function is epistatic to NCoR.

To determine the consequences of loss of PIAS1 or Ubc9 function with respect to occupancy of PPARγ and NCoR on the iNOS promoter, ChIP assays were carried out in primary macrophages transfected with control siRNAs or siRNAs directed against PIAS1 or Ubc9. Knockdown of PIAS1 expression prevented ligand-dependent recruitment of PPARγ to the iNOS promoter, but did not affect PPARγ recruitment to the positively-regulated CD36 promoter (FIG. 4d). Interestingly, knockdown of either PIAS1 or Ubc9 enabled the clearance of NCoR from the iNOS promoter following LPS stimulation in the presence of rosiglitazone (FIG. 4e), suggesting that a SUMOylation-dependent step is required for PPARγ to prevent corepressor clearance. PIAS1 itself does not appear to be recruited to the iNOS promoter, as it was not detected in ChIP assays using antibodies to endogenous PIAS1 in primary macrophages or epitope-tagged PIAS1 in transfected RAW264.7 cells.

To explore the potential role of SUMOylation in transrepression by other nuclear receptors and in other organisms, we evaluated the ability of the Drosophila nuclear receptor Tailless (tll) to negatively regulate innate immune responses in Schneider cells, which are functionally related to macrophages[53,54]. Drosophila possess an LPS-responsive pathway analogous to that found in vertebrates[55]. Two NF-κB-like pathways are activated in response to LPS in Drosophila, Imd and Toll, that ultimately lead to the transcriptional activation and expression of several anti-microbial peptides[55]. LPS primarily signals through Imd, inducing expression of the anti-microbial peptide, Attacin A, via the NF-κB homologue relish (FIG. 4f). LPS treatment stimulates the activity of an Attacin A-luciferase reporter gene by approximately 10-fold in Schneider cells, with overexpression of tll causing repression of this activity (FIG. 4g). A dsRNA directed against tll completely reversed its ability to repress Attacin A activation (FIG. 4g). This effect was specific to the tll dsRNA as other dsRNA molecules directed against four other non-relevant targets did not reverse the transrepression phenotype. Significantly, dsRNAs against the Drosophila homologs for PIAS1 (Suvar2-10), Ubc9, and HDAC3 were each found to reverse Tailless-dependent repression of Attacin A promoter activity (FIG. 4g). Conversely, tll was capable of repressing the response of the iNOS promoter to LPS in RAW264.7 macrophages (FIG. 8a). Furthermore, in vitro SUMOylation assays demonstrated that tll itself could be effectively SUMOylated by SUMO-1 and SUMO-3 conjugation (FIG. 8b).

Ligand-Dependent SUMOylation of PPARγ is Required for Transrepression Activity

Unlike the Drosophila nuclear receptors, which acted constitutively to repress LPS signaling, the actions of PPARγ are ligand-dependent. Recent reports have indicated that PPARγ can be SUMOylated within the N-terminal AF1 domain of PPARγ2 at K107 (equivalent to K77 of PPARγ1) and that this modification inhibits PPARγ activity on positively-regulated target genes[56]. Examination of the primary amino acid sequence of murine PPARγ. revealed an additional SUMOylation consensus sequence ψKXE/D[52] at K365 (corresponding to K367 in the human PPARγ sequence, FIG. 5a). Intriguingly, crystal structures of the apo and rosiglitazone-bound forms of PPARγ indicated that the primary amine group of K365 was oriented towards the interior of the LBD in the apo form, but solvent exposed in the rosiglitazone-bound form (FIG. 5a). A similar shift occurs in the structure of PPARγ bound to GW0072[42]. Because this amino group is the point of covalent attachment of SUMO, the PPARγ crystal structures suggested that K365 would be SUMOylated in a ligand-dependent manner. To test this hypothesis, K365 of PPARγ1 was mutated to arginine and the wild type and mutant proteins were tested for SUMOylation in vivo and in vitro (FIG. 5b). Wild-type PPARγ was found to exhibit a basal level of SUMOylation by Myc-tagged Sumo1 that was significantly enhanced following treatment with rosiglitazone (FIG. 5b). In contrast, the basal level of SUMOylation of PPARγ$^{K365R}$ was not enhanced by rosiglitazone treatment (FIG. 5b). Most of the ligand-independent SUMOylation was abolished by mutation of PPARγ K77 to arginine, consistent with previous findings[56]. Similar results were obtained using in vitro SUMOylation assays.

The potential effects of these mutations on interactions of PPARγ with PIAS1 were assessed by co-immunoprecipitation experiments in RAW264.7 macrophages. These experiments confirmed a ligand-induced interaction of wild-type PPARγ with PIAS1 at 30 min (FIGS. 3c, 5c), but also revealed a marked reduction in PIAS1 interaction by 60 minutes of treatment (FIG. 5c). The interactions of PPARγ$^{K77R}$ and PPARγ$^{K365R}$ with PIAS1 were also stimulated by rosiglitazone, but their dissociation at 60 min was less pronounced than wild-type PPARγ, suggesting that SUMOylation triggers release of PPARγ from PIAS1.

To determine the functional consequences of K77- and K365-dependent SUMOylation, the ability of each mutant to inhibit the iNOS promoter and/or transactivate a positively regulated PPARγ-dependent promoter were tested in RAW264.7 cells. PPARγ$^{K365R}$ was defective for inhibition of the iNOS promoter, while PPARγ$^{K77R}$ retained full transrepression activity (FIG. 5d). PPARγ$^{K77R}$ exhibited enhanced transactivation function, consistent with previous findings[56], while PPARγ$^{K365R}$ exhibited approximately the same activity as wild-type PPARγ on the positively regulated Aox-TK luciferase promoter (FIG. 5e). ChIP assays were next performed to investigate whether SUMOylation of PPARγ is required for its recruitment to the iNOS promoter. Wild-type PPARγ and PPARγ$^{K77R}$ were efficiently recruited to the iNOS promoter in response to rosiglitazone, while PPARγ$^{K365R}$ was not (FIG. 5f). In contrast, wild-type PPARγ and each of the PPARγ mutants were recruited to the positively regulated CD36 promoter (FIG. 5g). As a further pharmacological test of the role of PPAR 65R, we evaluated a ligand (GW1929) that stabilizes helix 12 in an active conformation but does not significantly alter the conformation of K365. Interestingly, this ligand exhibited strong transactivation activity but was a very weak repressor of LPS induced iNOS promoter activity.

A conserved SUMOylation-dependent pathway mediates transrepression by PPARγ

Figure 6A:
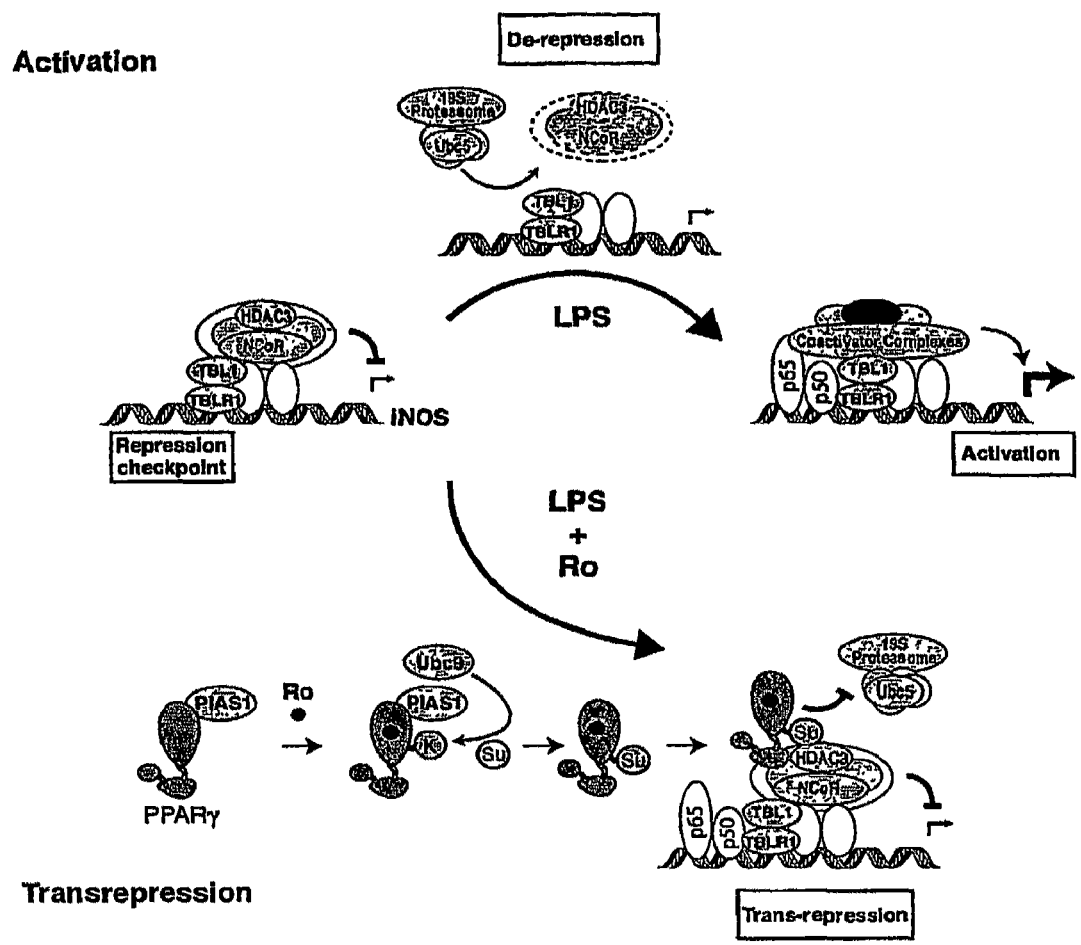
FIG. 6. 6A Illustrates the mechanism of PPARγ-dependent repression. Under basal conditions, an NCoR/HDAC3/TBL complex is associated with LPS target promoters such as iNOS. LPS induction results in clearance of the co-repressor complex in an ubiquitin/UbcH5-dependent manner, allowing for the recruitment of sequence-specific activators such as NF-κB and coactivator complexes necessary for the activation of the target promoter. In the presence of Ro, PPARγ K365 undergoes a conformational change enabling PIAS1-dependent SUMOylation. SUMOylated PPARγ subsequently translocates to the NcoR/HDAC3/TBL co-repressor complex, where it prevents UbcH5-dependent ubiquitylation and co-repressor clearance. 6B. shows mammalian two-hybrid assay in RAW264.7 cells, indicating that wild-type VP16-PPARγ interacts with Gal-DBD-NCoRΔIDC (NCOR amino acids 1-2277, without the IDC), but not Gal-DBD-NCoR IDC (the C-terminal nuclear receptor interaction motif of NCoR), in a ligand-dependent and Ubc9-dependent manner. 6C, siRNA directed against HDAC3 reduces but does not abolish recruitment of PPARγ to the iNOS promoter in primary macrophages, as demonstrated by ChIP assays. 6B and 6C show SUMOylation of PPARg promotes interaction with NCoR-HDAC3 complex.
Figure 6B:
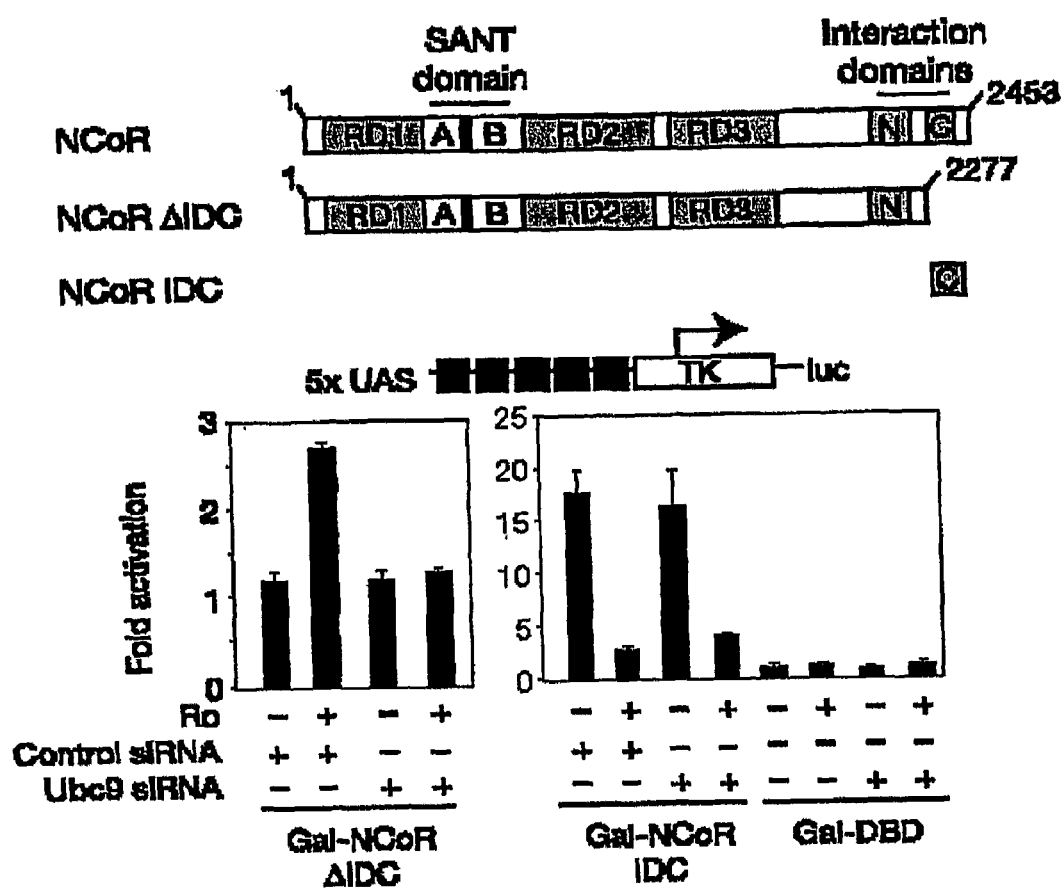
Figure 6C:
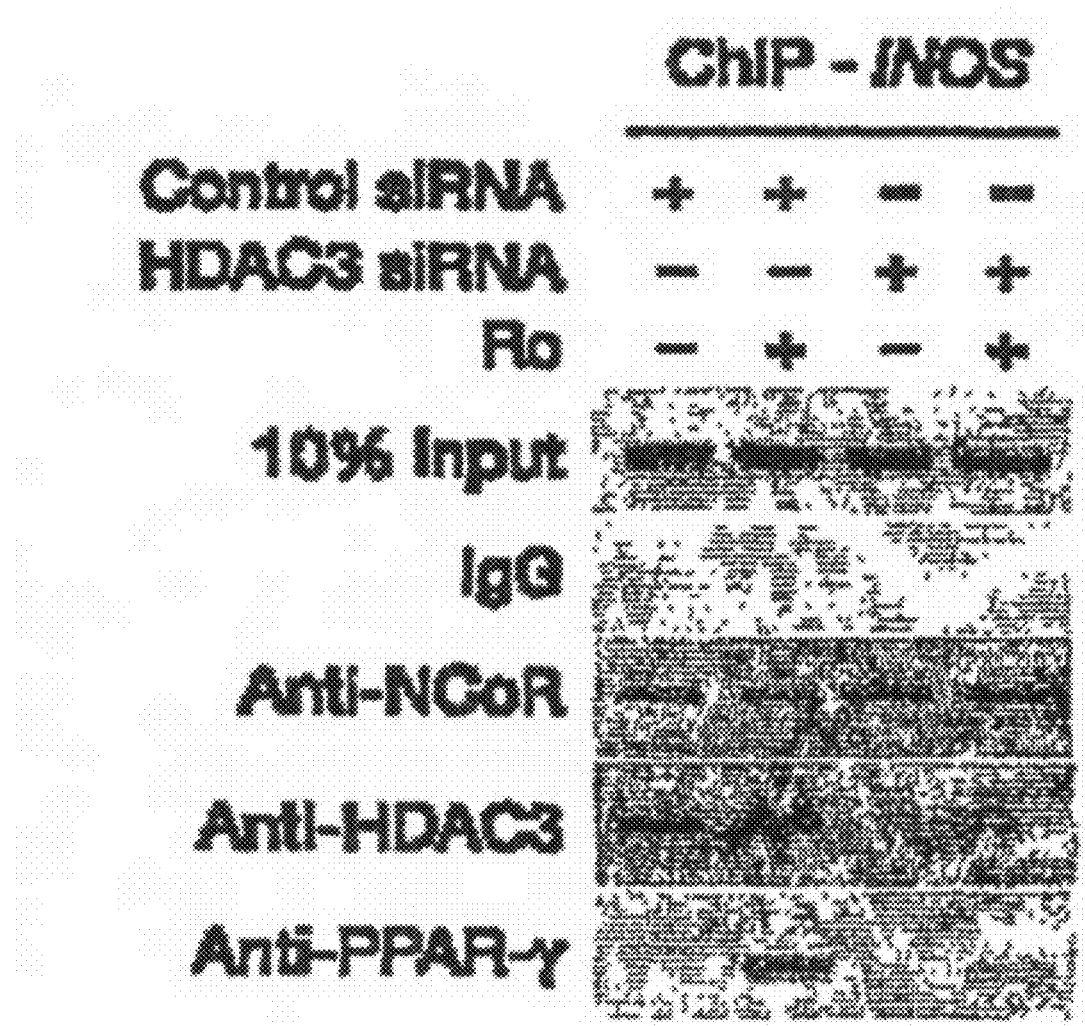

The present studies define a novel pathway mediating ligand-dependent transrepression of inflammatory response genes by PPARγ in macrophages (FIG. 6A). Genes subject to transrepression by this pathway are marked in the basal state by the presence of NCoR/HDAC3/TBL corepressor complexes. In the absence of a PPARγ agonist, LPS signaling results in the clearance of the NCoR and HDAC3 components of this complex in a TBL1-, TBLR1- and Ubc5-dependent manner, consistent with the clearance mechanism recently described for nuclear receptor target genes[36]. Activation is achieved by exchange of the NCoR corepressor complex for coactivator complexes that mediate transcriptional activation. The PPARγ-regulated transrepression pathway is initiated by ligand-induced interaction of PPARγ with PIAS1, resulting in site-specific SUMOylation of the ligand binding domain. This specific SUMOylation event targets PPARγ to NCoR complexes associated with LPS target genes and blocks the ability of Ubc5 to be recruited in response to LPS signals. As a result, NCoR complexes are not cleared from the promoter, resulting in a failure to relieve the repression checkpoint and maintaining these genes in a repressed state. The actual target of the NCoR complex recognized by SUMOylated PPARγ and the mechanism by which it prevents recruitment of Ubc5 remain to be established. It is also unclear at present whether SUMOylation affects recruitment of coactivators to PPARγ, as K365 is not part of the LXXLL docking surface. In concert, these findings expand the function of the NCoR repression checkpoint as a critical target of ligand-dependent negative regulation and provide a molecular explanation for how an agonist-bound nuclear receptor can be converted to a transcriptional repressor.

In macrophages, PPARγ appears to be SUMOylated on both K77 and K365. Based on our mutational analysis, this pattern of SUMOylation would be expected to impair transcriptional activation of positive target genes and enable repression of inflammatory response genes that are occupied by NCoR complexes. These findings are consistent with previous gene expression profiling experiments indicating that PPARγ primarily functions as a negative regulator of inflammatory gene expression in macrophages[17]. We speculate that a different pattern of SUMOylation predominates in other cell types, such as adipocytes, in which PPARγ functions as an effective activator of transcription. While the present studies suggest a quantitatively important role of PIAS1 in mediating SUMOylation of PPARγ at K365 in macrophages, we cannot exclude the possibility that other PIAS family members could contribute to this function in other contexts or cell types. PIAS1-null mice exhibit elevated levels of proinflammatory cytokines, consistent with established roles of PIAS1 as an inhibitor of STAT-mediated transcription and inhibition of p65-dependent gene expression[57,58]. The present studies suggest an additional mechanism that could contribute to this phenotype.

These studies have identified a transrepression pathway that links to cofactor turnover, but involves ligand-induced conformational changes of residues (i.e., K365 and surrounding amino acids) that are not part of previously defined docking interfaces for coactivators or corepressors. It will be of interest to define the extent to which this pathway is biologically utilized by PPARγ and other nuclear receptors and to determine how this mechanism can be exploited to develop new drugs for treatment of inflammatory and metabolic diseases.

Example 2

To determine how widely the SUMOylation/NCoR-dependent pathway is utilized by PPARγ to repress inflammatory response genes, microarray studies were performed in primary macrophages transfected with control siRNAs or siRNAs directed against NCoR mRNA. Knockdown of NCoR expression abolished the ability of rosiglitazone to repress 80% of the PPARγ-sensitive genes that were subject to repression in macrophages transfected with control siRNAs. Since NCoR-dependence for transrepression is tightly linked to SUMOylation-dependence, this result indicates that the SUMOylation pathway is the major pathway mediating anti-inflammatory effects of PPARγ in macrophages.

Figure 9:
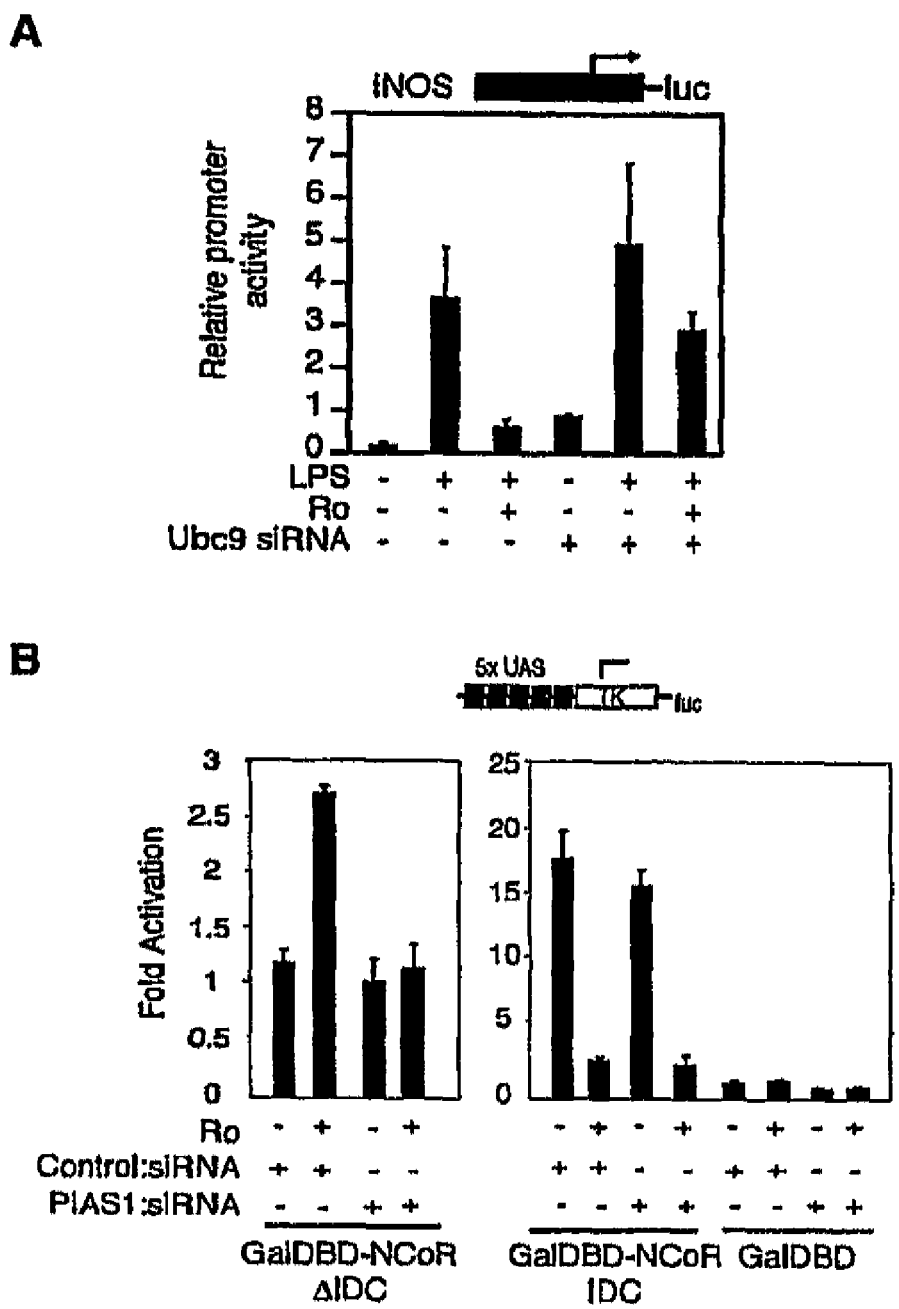
FIG. 9. Screening assays. Panel A illustrates a transient transfection assay. Panels B and C illustrates mammalian two-hybrid assay.
Figure 9:
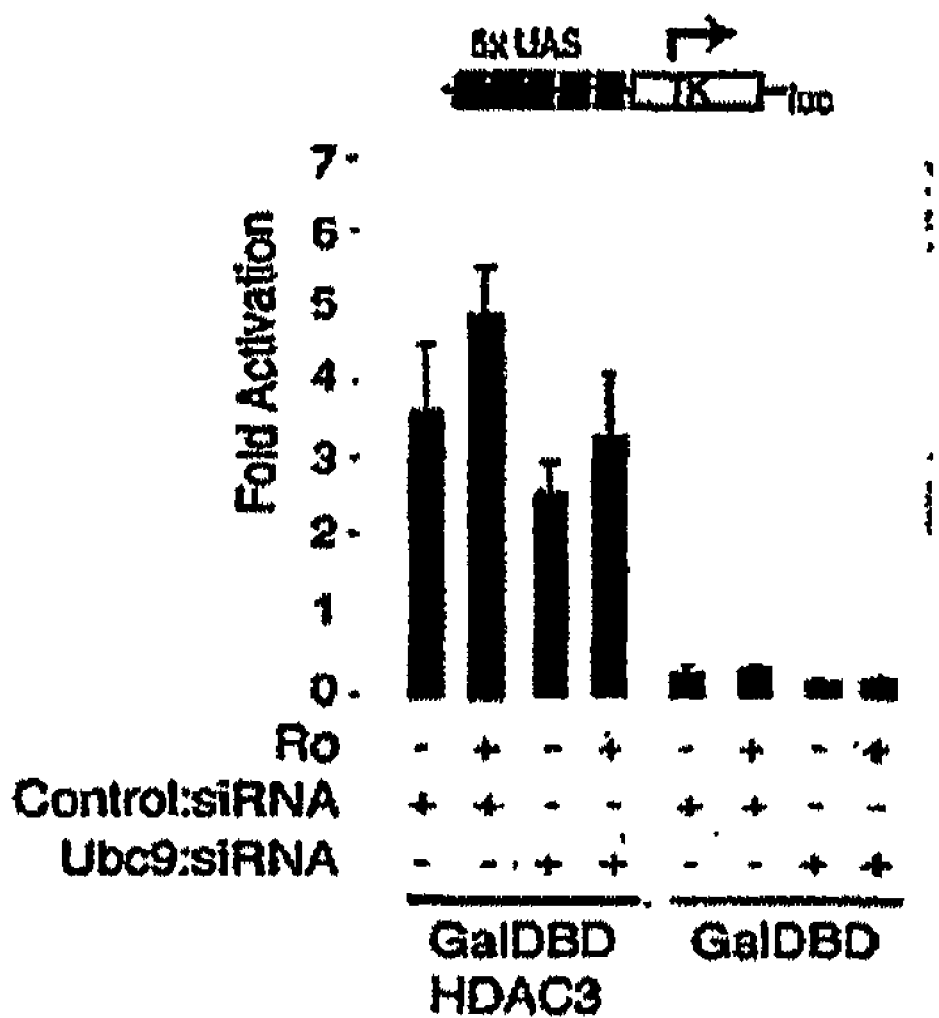

Two types of screening assays were explored to provide additional evidence for screening strategies for PPARγ ligands that specifically promote entry into the SUMOylation-dependent transrepression pathway, Panel A of FIG. 9 illustrates a transient transfection assay in which the ability of a PPARγ ligand, in this case rosiglitazone, is tested for its ability to repress transcriptional activation of the iNOS promoter in the presence or absence of an siRNA directed against the SUMO E2 ligase, Ubc9. RAW264.7 cells were transfected with the iNOS reporter, PPARγ expression plasmid and control or Ubc9-siRNA. 36 h post-transfection cells were pretreated with Ro for 1 h and LPS for 6 h prior to assay of luciferase activity. Repression of iNOS activation in the presence of control siRNA and reversal of this repression by the Ubc9 siRNA provides a highly specific signature of SUMOylation-dependent repression that is scalable to a high throughput screen.

As a second strategy, the ability of a PPARγ ligand to promote interaction of constitutively active VP16-PPARγ with NCoR and HDCA3 in a SUMOylation-dependent manner was tested by mammalian two-hybrid assay (FIGS. 9B and 9C). Macrophages were transfected with mammalian two-hybrid reporter (5X-UAS TK-luciferase), VP-16 PPARγWT and either GalDBD-NCoR IDC or GalDBD-NCoR ΔIDC (NCoR a.a. 1-2277 without IDC). The NCoR IDC interacts with unliganded nuclear receptors and this interaction is dismissed by agonist binding to the nuclear receptor ligand binding domain. SUMOylation-dependent interaction of PPARγ does not utilize this domain. Therefore, this domain was removed, to assess ligand and SUMOylation-dependent interactions with the remainder of the NCoR protein (NCOR ΔIDC). Control or PIAS1 siRNA was co-transfected and cells were cultured with 0.01 μM trichostatin A (TSA) prior to treatment with 1 mM Ro to block HDAC3 activity associated with NCoR ΔIDC. Cells were assayed for luciferase activity 16 hours after Ro treatment. The ability of rosiglitazone to induce luciferase activity in a PIAS1-dependent manner in the GalDBD-NCoR ΔIDC-transfected cells indicates a SUMOylation-dependent interaction with NCoR ΔIDC. This assay thus directly assesses the immediate consequence of ligand-dependent SUMOylation and is also scaleable to a high throughput screen.

Example 3

This example demonstrates that the PPARγ mechanism extends to other nuclear receptors.
Methods
Cell Culture Thioglycollate-elicited macrophages were isolated by peritoneal lavage 3 days following peritoneal injection of 2.5 ml 3% thioglycollate (DIFCO). Cells were plated in RPMI medium 1640 and 10% fetal bovine serum. After 5 h the medium was removed and cells were fed with fresh medium. For RNAi experiments, smart-pool siRNAs (Dharmacon) against NCoR and Ubc9 were transfected into primary macrophages using lipofectamine 2000 (Invitrogen), incubated for 48 h and validated by Q-PCR and Western Blotting. LPS (Sigma) was used at a concentration of 1 μg/ml and GW3965 (obtained under MTA from GlaxoSmithKline) was used at a concentration of 1 μM.
Transient Transfection The RAW264.7 mouse macrophage cell line was transiently transfected with iNOS or ABCA1 promoters directing luciferase expression, pCMXhLYRα, FLAGhLXRβ, and their mutants. For transrepression experiments, wildtype LXRα and LXRβ or LXR mutants were transfected at a 3:1 (LXR to reporter plasmid) ratio using Superfect reagent (Qiagen). For siRNA experiments, RAW264.7 cells were transfected with siRNAs (40 nM) using Superfect reagent for 48 h before activation with LXR ligands and LPS induction. In all transfections, cells were treated with 1 μM GW3965 and then stimulated with 1 μg/ml of LPS and assayed for luciferase activity 12 h later.
Chromatin Immunoprecipitation Assays.

For each experimental condition, 20×10$^6$ primary macrophages were used. Cells were pre-treated with 1 μM GW3965 (1 h) and stimulated with 1 μg/ml LPS (1 h) before crosslinking for 10 min with 1% formaldehyde. Crosslinked adducts were resuspended and sonicated resulting in DNA fragments of 300-900 bp. Anti-LXR (Calbiochem) or anti-NCoR (Affinity Bioreagents) antibodies were used. Protein-bound, immunoprecipitated DNA was reverse cross-linked at 65° C. overnight and then purified using PCR purification Kit (Qiagen). A 150-bp region of the iNOS promoter was amplified by real time PCR spanning the most proximal NF-κB site to the start of transcription.
RNA Isolation, Real Time PCR Total RNA (isolated by RNeasy kit, Qiagen) was prepared from primary macrophages pretreated with 1 μM GW3965 (2 h) before 1 μg/ml LPS stimulation (6 h). One microgram of total RNA was used for CDNA synthesis, and 1 μl of cDNA was used for real time PCR using iNOS or inflammatory-gene-specific primers.
SUMOylation Assays.

For in vivo SUMOylation experiments, whole protein extract was prepared from HeLa cells transfected with FLAG-tagged wild-type LXRα and LXRβ or SUMO point mutants and Myc-tagged SUMO-1 or SUMO-2. Extracts were resolved by SDS-PAGE and immunoblotted using anti-FLAG or anti-Myc antibodies.

To extend the initial findings regarding the SUMOylation and NCoR-dependent pathway mediating repression of inflammatory response genes by PPARγ, —the utility of this pathway by other receptors was assessed. The Liver X receptors (LXRs) α and β have also been reported to inhibit inflammatory gene expression, but molecular mechanisms have not been established. Therefore LXRα and LXRβ were selected for this analysis, using the LXRα/β-specific ligand GW3965 as an agonist. Initial studies utilized LPS induction of the inducible nitric oxide synthase (iNOS) gene in primary macrophages and the RAW264.7 macrophage cell line as a model systems, as previous studies have demonstrated that this gene is subject to repression by LXR agonists in these cells.

Figure 10:
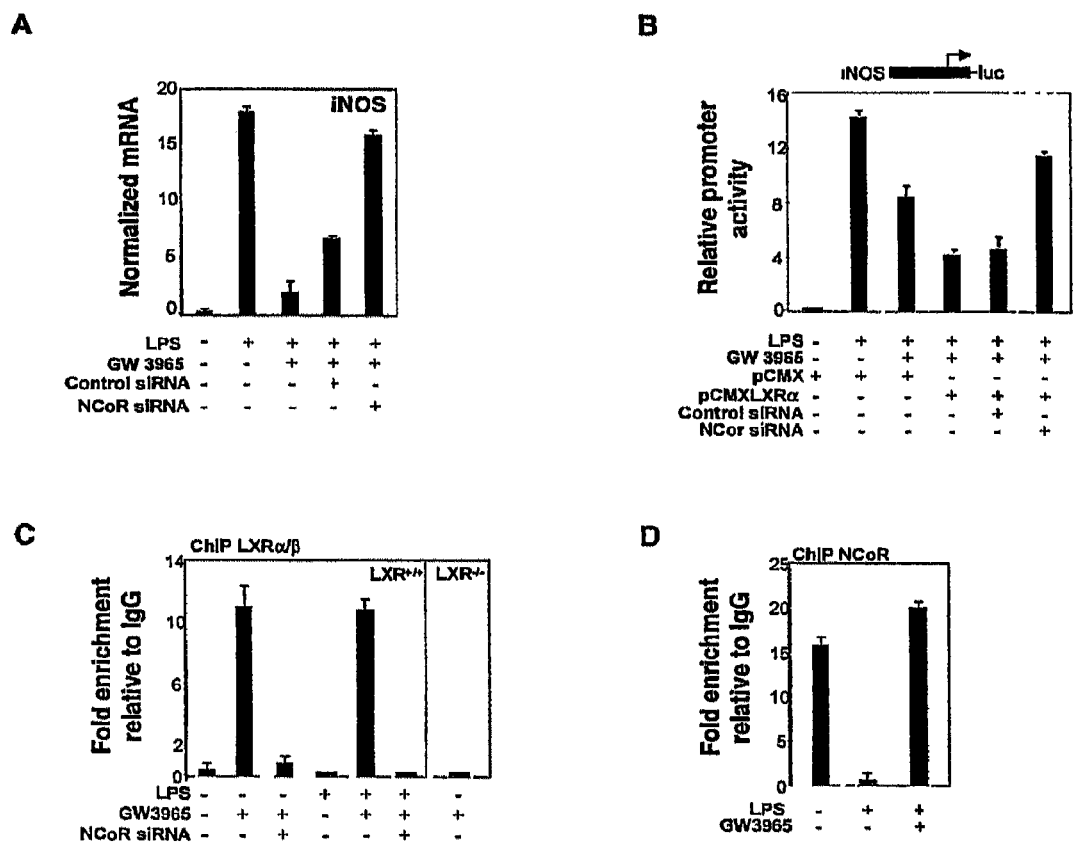
FIG. 10. Real-time quantitative PCR (10a), luciferase gene activity (10b) and chromatin immunoprecipitation (10c and 10d) demonstrate that ligand-dependent transrepression of the iNOS gene by LXRs require NCoR.

FIG. 10 illustrates experiments demonstrating that ligand-dependent transrepression of the iNOS gene by LXRs requires NCoR. Panels A and B of FIG. 10 demonstrate that inhibition of NCoR expression using a NCoR-specific siRNA abolishes LXR ligand (GW3965)-dependent repression of LPS-induced iNOS expression in peritoneal macrophages (A) and iNOS promoter activation (B) in RAW264.7 cells transfected with expression vector for LXRα (B). Macrophages were transfected with siRNA for 48 h and then stimulated with LPS (1 mg/ml) for 6 h in the absence or presence of LXR ligand (GW3965, 1 μM). iNOS expression in peritoneal macrophages was evaluated by real-time quantitative PCR and iNOS promoter activation in RAW264.7 was evaluated by luciferase assay. Panel C of FIG. 10 illustrates chromatin immunoprecipitation (CHIP) assays demonstrating ligand-dependent and NCoR-dependent LXR recruitment on the iNOS promoter. Primary macrophages were treated with LPS (1 mg/ml) with or without the LXR ligand (GW3965, 1 μM) for 1 h. ChIP assay was performed with antibody against LXR (both isoforms, α and β and control IgG. Immunoprecipitated DNA was analyzed by real-time quantitative PCR using primers specific for the iNOS-promoter. Cell lysates from LXR$^{-/-}$ mice were used as negative control for specificity of the LXR antibody. panel D of FIG. 10 illustrates a representative experiment indicating that LXR ligand inhibits LPS-stimulated release of NCoR from the iNOS promoter as shown by ChIP assay in peritoneal macrophages, treated as described in Panel C of FIG. 10. In each case, error bars represent standard deviations. These results for LXRs are in complete accord with the results of studies of PPARγ on the iNOS promoter, in which PPARγ was recruited to the iNOS promoter in a ligand- and NCoR-dependent manner and PPARγ agonists prevented the LPS dependent clearance of NCoR from this promoter.

Figure 11:
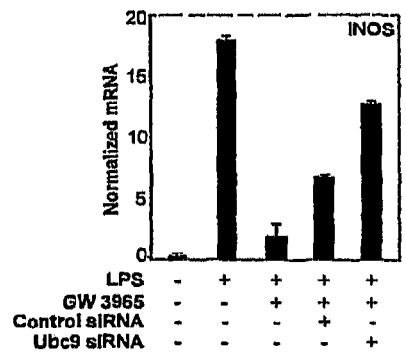
FIG. 11. Real-time quantitative PCR (11a), luciferase gene activity (11b and 11c), and chromatin immunoprecipitation (11d and 11e) demonstrate that LXR-dependent transrepression is SUMOylation dependent.
Figure 11:
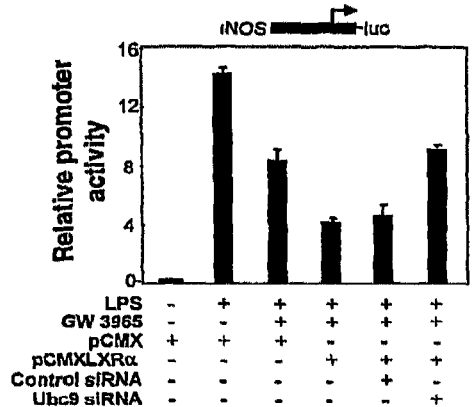
Figure 11:
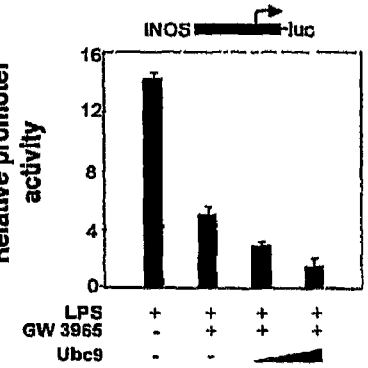
Figure 11:
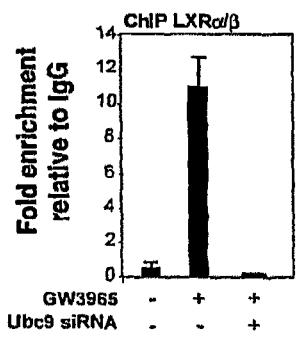
Figure 11:
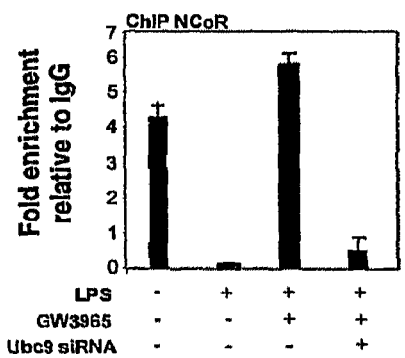

FIG. 11 illustrates experiments indicating that LXR-dependent transrepression is SUMOylation dependent. In panels A and B of FIG. 11, partial knockdown of Ubc9 by a Ubc9-specific siRNA significantly impairs LXR ligand (GW3965)-dependent repression of LPS-induced iNOS expression (A) and iNOS promoter activation (B) in peritoneal macrophages (A) and in RAW264.7 cells transfected with expression vector for LXRα (B). Macrophages were transfected with Ubc9 siRNA or non specific siRNA (control siRNA) for 48 h and then stimulated with LPS (1 mg/ml) for 6 h in the absence or presence of LXR ligand (GW3965, 1 mM). In panel C of FIG. 11, Ubc9 overexpression increases LXR ligand-dependent transrepression of the iNOS promoter. RAW264.7 cells were transfected with expression vector for LXRα and increasing amounts of Ubc9 expression vector and then stimulated with LXR ligand (GW3965, 1 mM) followed by LPS (1 mg/ml) for 6 h. In panels D and E of FIG. 11, siRNA directed against Ubc9 prevents LXR recruitment (D) and abolished the ability of the LXR agonist to inhibit NCoR clearance (E) from iNOS promoter as shown by ChIP. Primary macrophages were treated with LPS (1 mg/ml) with or without the LXR ligand (GW3965, 1 mM) for 1 h. ChIP assay was performed with antibody against LXR or NCoR and control IgG. Immunoprecipitated DNA was analyzed by real-time quantitative PCR using primers specific for the iNOS-promoter. Error bars represent standard deviations. These results are also fully in accord with the mechanism described for PPARγ, in which PPARγ binding to the iNOS promoter and repression of LPS-dependent induction required the Ubc9 SUMO E2 ligase.

Figure 12:
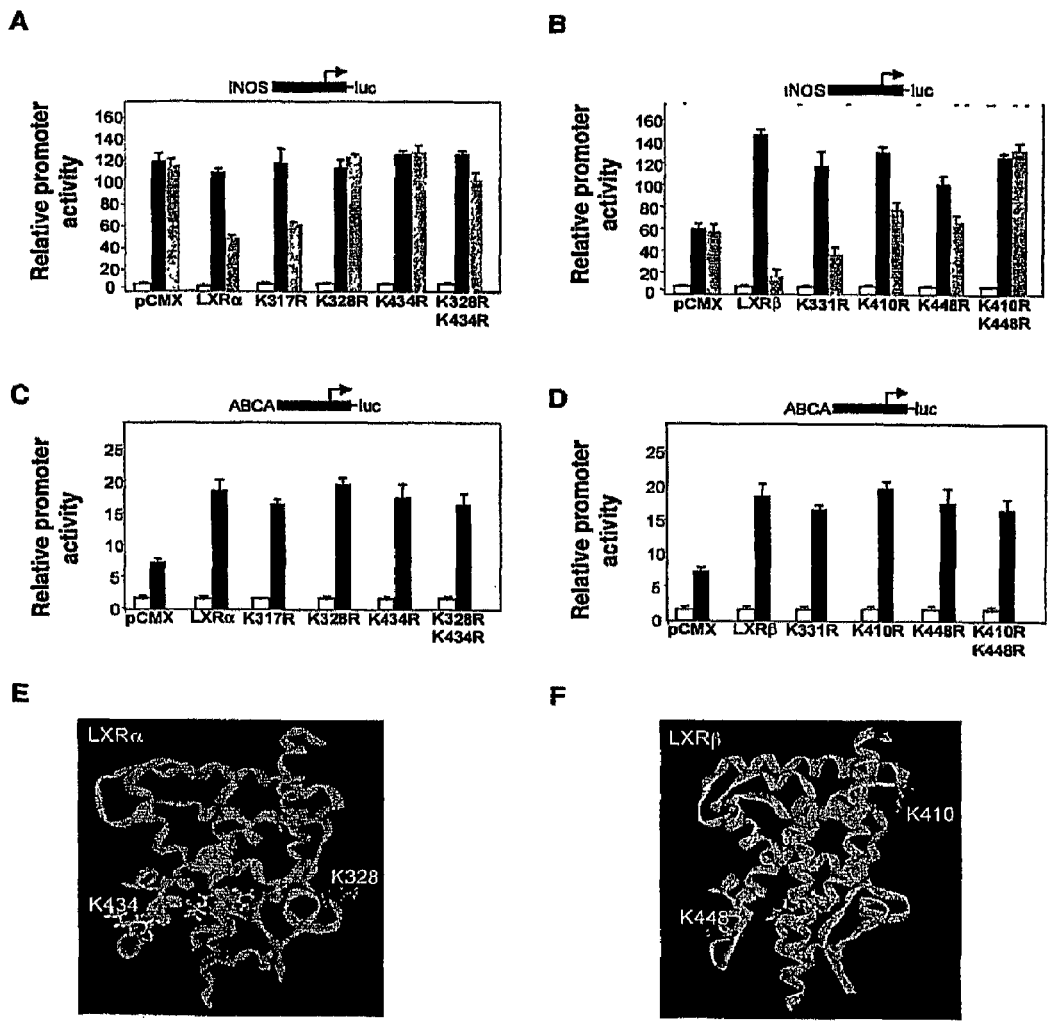
FIG. 12. Luciferase activity (12a-12d) demonstrate that specific lysine residues that are potential SUMO acceptor sites in LXRα and LXRβ are required for transrepression but not for activation. 12e and 12f illustrate crystal structures of the ligand-bound form of LXRα (E) and LXRβ (F), indicating the location of K328, K434 (E) and K410, K448 (F) in the ligand-binding domains of each receptor.

The experiments illustrated in FIG. 12 demonstrate that specific lysine residues that are potential SUMO acceptor sites in LXRα and LXRβ are required for transrepression but not for transactivation. Panels A and B of FIG. 12 illustrate the effects of specific lysine mutations on the ability of LXRα (A) and LXRβ (B) to repress iNOS activation. Mutation of K328 or K434 to ariginine abolish the ability of LXRα to repress iNOS induction. In the case of LXRβ, mutation of K410 and K448 each partially impair transrepression activity, and the double mutant fully reverses transrepression. Panels C and D of FIG. 12 illustrate that lysine mutations that abolish transrepression do not impair ligand-dependent transactivation of a positively regulated target gene. RAW264.7 cells were transfected with reporter vectors iNOS-luc (A,B) or ABCA1-luc (C,D) and with expression vectors for LXRα (A,C) or LXRβ (B,D) wild type or mutated in specific lysine residues as indicated (A,C: K317, K328, K434, B,D:K331, K410, K448). 24 h after transfection, cells were treated with DMSO (white bars) or with LPS (1 mg/ml) for 12 h in the absence (black bars) or presence of LXR ligand (GW3965, 1 mM, dashed bars). Error bars represent standard deviations. Panels E and F of FIG. 12 illustrate crystal structures of the ligand-bound form of LXRα (E) and LXRβ (F), indicating the location of K328, K434 (E) and K410, K448 (F) in the ligand-binding domains of each receptor. These results are in general agreement with studies of PPARγ, which demonstrated that mutations of SUMO acceptor sites in the ligand binding domain abolished transrepression activity without affecting transactivation activity, although the specific lysine residues are different. Consistent with this, LXRs do not use PIAS1 as a SUMO E3 ligase, which is required for PPARγ SUMOylation. The SUMO E3 ligase(s) specific for LXRs remain to be identified.

Figure 13:
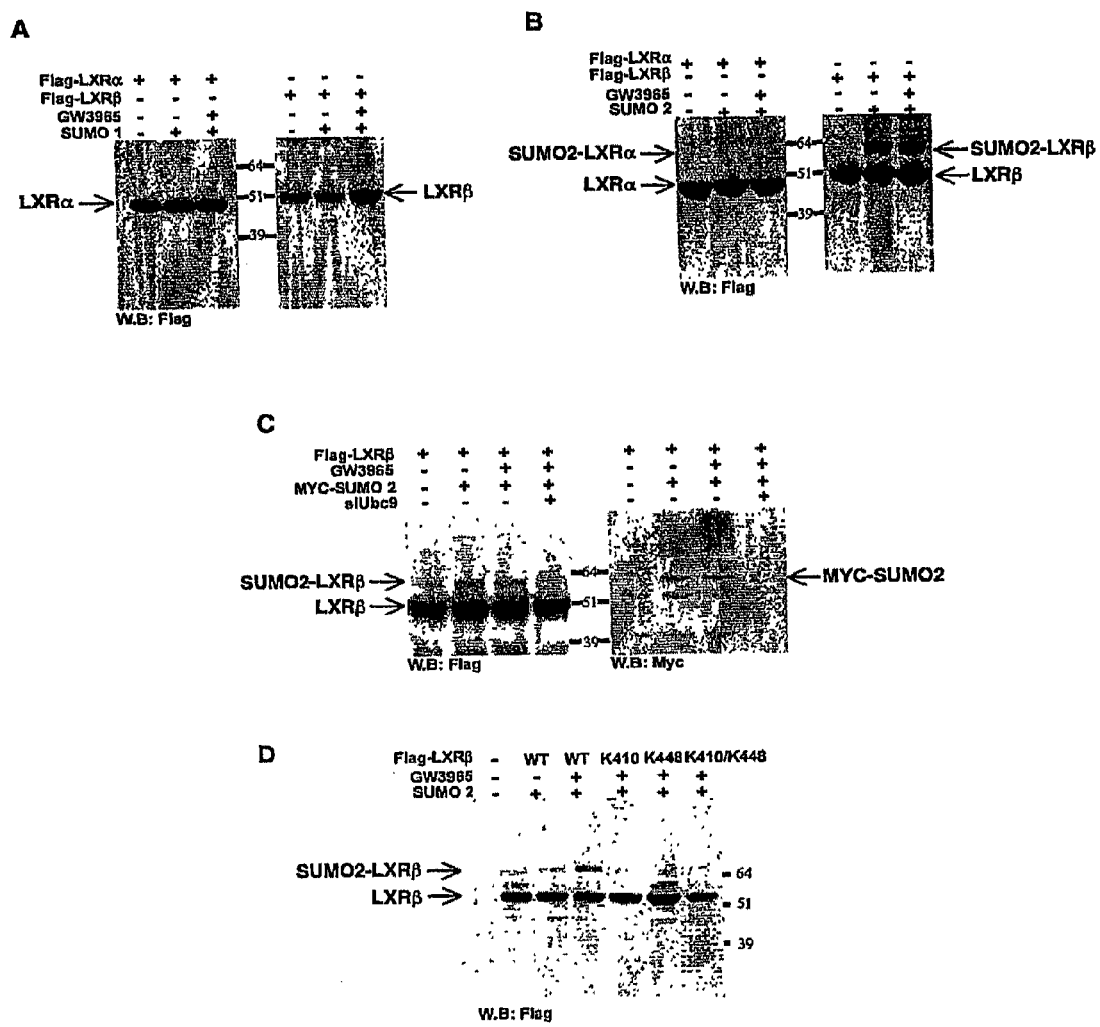
FIG. 13. immunoblots (13a-13d) illustrate cell-based SUMOylation assays demonstrating that LXRα and LXRβ are preferentially SUMOylated by SUMO-2.

FIG. 13 illustrates cell-based SUMOylation assays demonstrating that LXRα and LXRα are preferentially SUMOylated by SUMO-2. Panel A of FIG. 13 illustrates that LXRβ, but not LXRα, is weakly SUMOylated by SUMO-1. Hela cells were transfected with FLAG-LXRα or FLAG-LXRβ and with Ubc9 and SUMO-1 expression vector. Whole cell lysates were immunoblotted for FLAG-tag. Panel B of FIG. 13 illustrates that LXRβ and to lesser extent LXRα, are SUMOylated by SUMO-2 as shown by SUMOylation assay in vivo in HeLa cells described in A. Panel C of FIG. 13 demonstrates that knock down of Ubc9 by specific siRNA blocks the SUMO-2 conjugation of LXRβ. Hela cells were transfected with FLAG-LXRb and with Ubc9 and MYC-SUMO-2 expression vectors. Whole cell lysates were immunoblotted for FLAG-tag and SUMO MYC-tag. Panel D of FIG. 13 illustrates that SUMOylation of LXRβ occurs at K410 and K448 as demonstrated by SUMOylation assay in Hela cells transfected with WT FLAG-LXRβ or FLAG-mutants K410, K448 or double mutants K410/K448 as indicated. In concert, these experiments indicate that the putative SUMOylation sites that are shown to be required for transrepression activity in FIG. 12 are also required for SUMOylation by SUMO2. These observations are in general agreement with findings for PPARγ, except that PPARγ appears to be preferentially SUMOylated by SUMO1. This difference is also consistent with the observation that PPARγ and LXRs use different SUMO E3 ligases.

Figure 14:
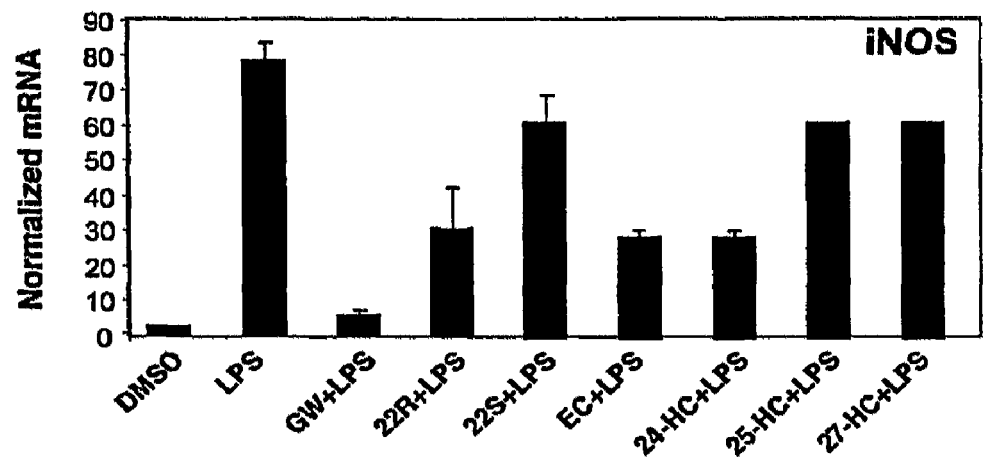
FIG. 14. Real-time PCR (upper and lower panels) illustrates the ability of natural LXR ligands to repress iNOS activation and induce expression of ABCA1 gene in primary macrophages.
Figure 14:
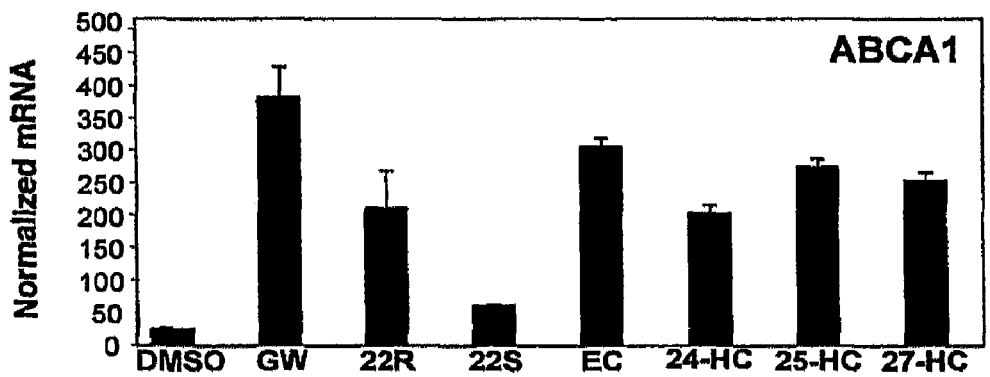

FIG. 14 illustrates the ability of natural LXR ligands to repress iNOS activation and induce expression of the ABCA1 gene in primary macrophages. 22R-hydroxycholesterol, 24(S), 25-epoxycholesterol and 24-hydroxycholesterol both repress iNOS activation and induce ABCA1 expression, although less potently than the synthetic ligand, GW3965 (GW). In contrast, 25 hydroxycholesterol and 27-hydroxycholesterol activate ABCA1, but do not repress iNOS activation, indicating that activation and transrepression activities can be chemically separated. Primary mouse peritoneal macrophages were treated in the upper panel with LPS and the indicated ligands and harvested for real time PCR analysis of iNOS expression 6 h later. In the lower panel, cells were treated with the indicated ligands for 18 hours and harvest for real time PCR analysis of ABCA1 expression. GW3965 was used at a concentration of 1 μM. The oxysterols were used at a concentration of 5 μM.

In concert, these studies indicate that the SUMOylation-dependent pathway initially identified to mediate transrepression of inflammatory responses by PPARγ is also utilized by LXRα and LXRβ. These findings suggest that transcription factor SUMOylation may be a common strategy in transrepression by many nuclear receptors, and perhaps other classes of sequence-specific transcription factors.

REFERENCES

1. Spiegelman, B. M. PPAR-gamma: adipogenic regulator and thiazolidinedione receptor. *Diabetes* 47, 507-14 (1998).
2. Lehmann, J. M. et al. An antidiabetic thiazolidinedione is a high affinity ligand for peroxisome proliferator-activated receptor gamma (PPARgamma). *J Biol. Chem.* 270, 12953-12956 (1995).
3. Willson, T. M. et al. The structure-activity relationship between peroxisome proliferator-activated receptor gamma agonism and the antihyperglycemic activity of thiazolidinediones. *J. Med. Chem.* 39, 665-8 (1996).
4. He, W. et al. Adipose-specific peroxisome proliferator-activated receptor gamma knockout causes insulin resistance in fat and liver but not in muscle. *Proc Natl Acad Sci USA* 100, 15712-7 (2003).
5. Hevener, A. L. et al. Muscle-specific Pparg deletion causes insulin resistance. *Nat Med* 9, 1491-7 (2003).
6. Norris, A. W. et al. Muscle-specific PPARgamma-deficient mice develop increased adiposity and insulin resistance but respond to thiazolidinediones. *J Clin Invest* 112, 608-18 (2003).

7. Gavrilova, O. et al. Liver peroxisome proliferator-activated receptor gamma contributes to hepatic steatosis, triglyceride clearance, and regulation of body fat mass. *J Biol Chem* 278, 34268-76 (2003).
8. Picard, F. & Auwerx, J. PPAR(gamma) and glucose homeostasis. *Annu Rev Nutr* 22, 167-97 (2002).
9. Weisberg, S. P. et al. Obesity is associated with macrophage accumulation in adipose tissue. *J Clin Invest* 112, 1796-808 (2003).
10. Xu, H. et al. Chronic inflammation in fat plays a crucial role in the development of obesity-related insulin resistance. *J Clin Invest* 112, 1821-30 (2003).
11. Pittas, A. G., Joseph, N. A. & Greenberg, A. S. Adipocytokines and insulin resistance. *J Clin Endocrinol Metab* 89, 447-52 (2004).
12. Li, A. et al. Peroxisome proliferator-activated receptor γ ligands inhibit development of atherosclerosis in LDL receptor-deficient mice. *J. Clin. Invest.* 106, 523-531 (2000).
13. Collins, A. R. et al. Troglitazone inhibits formation of early atherosclerotic lesions in diabetic and nondiabetic low density lipoprotein receptor-deficient mice. *Arterioscler. Thromb. Vasc. Biol.* 21, 365-71. (2001).
14. Chen, Z. et al. Troglitazone inhibits atherosclerosis in apolipoprotein E-knockout mice: pleiotropic effects on CD36 expression and HDL. *Arterioscler. Thromb. Vasc. Biol.* 21, 372-7. (2001).
15. Claudel, T. et al. Reduction of atherosclerosis in apolipoprotein E knockout mice by activation of the retinoid X receptor. *Proc. Natl. Acad. Sci. U.S.A.* 98, 2610-5. (2001).
16. Chawla, A. et al. A PPAR gamma-LXR-ABCA1 pathway in macrophages is involved in cholesterol efflux and atherogenesis. *Mol. Cell.* 7, 161-71. (2001).
17. Welch, J. S., Ricote, M., Akiyama, T. E., Gonzalez, F. J. & Glass, C. K. PPARgamma and PPARdelta negatively regulate specific subsets of lipopolysaccharide and IFN-gamma target genes in macrophages. *Proc Natl Acad Sci USA* 100, 6712-7 (2003).
18. Jonat, C., Rahmsdorf, H. J., Park, K.-K., Ponta, H. & Herrlich, P. Anti-tumor promotion and antiinflammation: down-modulation of AP-1 (Fos/Jun) activity by glucocorticoid hormone. *Cell* 62, 1189-1204 (1990).
19. Schüle, R. et al. Functional antagonism between a coprotein c-Jun and the glucocorticoid receptor. *Cell* 62, 1217-1226 (1990).
20. Yang-Yen, H.-F. et al. Transcriptional interference between c-Jun and the glucocorticoid receptor: mutual inhibition of DNA binding due to direct protein-protein interaction. *Cell* 62, 1205-1215 (1990).
21. Auphan, N., DiDonato, J. A., Rosette, C., Helmberg, A. & Karin, M. Immunosuppression by glucocorticoids: inhibition of NF-κB activity through induction of IκB Synthesis. *Science* 270, 286-290 (1995).
22. Ricote, M., Li, A. C., Willson, T. M., Kelly, C. J. & Glass, C. K. The peroxisome proliferator-activated receptor-γ is a negative regulator of macrophage activation. *Nature* 391, 79-82 (1998).
23. Jiang, C., Ting, A. T. & Seed, B. PPAR-gamma agonists inhibit production of monocyte inflammatory cytokines. *Nature* 391, 82-86 (1998).
24. Sheppard, K. A. et al. Nuclear integration of glucocorticoid receptor and nuclear factor-kappaB signaling by CREB-binding protein and steroid receptor coactivator-1. *J Biol Chem* 273, 29291-4. (1998).
25. Ito, K., Barnes, P. J. & Adcock, I. M. Glucocorticoid receptor recruitment of histone deacetylase 2 inhibits interleukin-1beta-induced histone H4 acetylation on lysines 8 and 12. *Mol Cell Biol* 20, 6891-903. (2000).
26. Nissen, R. M. & Yamamoto, K. R. The glucocorticoid receptor inhibits NFkappaB by interfering with serine-2 phosphorylation of the RNA polymerase II carboxy-terminal domain. *Genes Dev* 14, 2314-29. (2000).
27. De Bosscher, K., Vanden Berghe, W. & Haegeman, G. The interplay between the glucocorticoid receptor and nuclear factor-kappaB or activator protein-1: molecular mechanisms for gene repression. *Endocr Rev* 24, 488-522 (2003).
28. Chen, J. D. & Evans, R. M. A transcriptional co-repressor that interacts with nuclear hormone receptors. *Nature* 377, 454-457 (1995).
29. Horlein, A. J. et al. Ligand-independent repression by the thyroid hormone receptor mediated by a nuclear receptor co-repressor. *Nature* 377, 397-404 (1995).
30. Glass, C. K. & Rosenfeld, M. G. The coregulator exchange in transcriptional functions of nuclear receptors. *Genes and Dev.* 14, 121-141 (2000).
31. Guenther, M., Lane, W., Fischle, W., Verdin, E. & Lazar, M. A Core SMRT corepressor complex containing HDAC3 and TBL1, a WD40-repeat protein linked to deafness. *Genes and Development* 14, 1048-1057 (2000).
32. Li, J. et al. Both corepressor proteins SMRT and N-CoR exist in large protein complexes containing HDAC3. *EMBO J* 19, 4342-4350 (2000).
33. Zhang, J., Kalkum, M., Chait, B. T. & Roeder, R. G. The N-CoR-HDAC3 nuclear receptor corepressor complex inhibits the JNK pathway through the integral subunit GPS2. *Mol Cell* 9, 611-23. (2002).
34. Yoon, H. G. et al. Purification and functional characterization of the human N-CoR complex: the roles of HDAC3, TBL1 and TBLR1. *Embo J* 22, 1336-46 (2003).
35. Perissi, V., Aggarwal, A., Glass, C. K., Rose, D. W. & Rosenfeld, M. G. A corepressor/coactivator exchange complex required for transcriptional activation by nuclear receptors and other regulated transcription factors. *Cell* 116, 511-26 (2004).
36. Ogawa, S. L. J. J., K.; Sawka-Verhelle, D.; Perissi, V.; Sasik, R.; Rose, D. W.; Johnson, R. S.; Rosenfeld, M. G.; and Glass, C K. An NCoR transcriptional checkpoint controlling AP-1-dependent gene networks required for macrophage activation. *Proct. Natl. Acad. Sci. USA*. 101, 14461-14466 (2004).
37. Hoberg, J. E., Yeung, F. & Mayo, M. W. SMRT Derepression by the IkappaB Kinase alpha; A Prerequisite to NF-kappaB Transcription and Survival. *Mol Cell* 16, 245-55 (2004).
38. Kuhlencordt, P. J., Chen, J., Han, F., Astern, J. & Huang, P. L. Genetic deficiency of inducible nitric oxide synthase reduces atherosclerosis and lowers plasma lipid peroxides in apolipoprotein E-knockout mice. *Circulation* 103, 3099-104 (2001).
39. Perreault, M. & Marette, A. Targeted disruption of inducible nitric oxide synthase protects against obesity-linked insulin resistance in muscle. *Nat Med* 7, 1138-43 (2001).
40. Lowenstein, C. J. et al. Macrophage nitric oxide synthase gene: two upstream regions mediate induction by interferon gamma and lipopolysaccharide. *Proc Natl Acad Sci USA* 90, 9730-4 (1993).
41. Oberfield, J. L. et al. A peroxisome proliferator-activated receptor gamma ligand inhibits adipocyte differentiation. *Proc Natl Acad Sci USA* 96, 6102-6 (1999).
42. Tontonoz, P., Nagy, L., Alvarez, J. G. A., Thomazy, V. A. & Evans, R. M. PPARγ promotes monocyte/macrophage differentiation and uptake of oxidized LDL. *Cell* 93, 241-252 (1998).

43. Liu, B. et al. Inhibition of Stat1-mediated gene activation by PIAS1. *Proc Natl Acad Sci USA* 95, 10626-31 (1998).
44. Jackson, P. K. A new RING for SUMO: wrestling transcriptional responses into nuclear bodies with PIAS family E3 SUMO ligases. *Genes Dev* 15, 3053-8. (2001).
45. Tallec, L. P. et al. Protein inhibitor of activated signal transducer and activator of transcription 1 interacts with the N-terminal domain of mineralocorticoid receptor and represses its transcriptional activity: implication of small ubiquitin-related modifier 1 modification. *Mol Endocrinol* 17, 2529-42 (2003).
46. Janne, O. A. et al. Androgen-receptor-interacting nuclear proteins. *Biochem Soc Trans* 28, 401-5 (2000).
47. Tan, J. et al. Protein inhibitor of activated STAT-1 (signal transducer and activator of transcription-1) is a nuclear receptor coregulator expressed in human testis. *Mol Endocrinol* 14, 14-26 (2000).
48. Kotaja, N., Karvonen, U., Janne, O. A. & Palvimo, J. J. PIAS proteins modulate transcription factors by functioning as SUMO-1 ligases. *Mol Cell Biol* 22, 5222-34 (2002).
49. Ling, Y. et al. Modification of de novo DNA methyltransferase 3a (Dnmt3a) by SUMO-1 modulates its interaction with histone deacetylases (HDACs) and its capacity to repress transcription. *Nucleic Acids Res* 32, 598-610 (2004).
50. Nishida, T. & Yasuda, H. PIAS1 and PIASxalpha function as SUMO-E3 ligases toward androgen receptor and repress androgen receptor-dependent transcription. *J Biol Chem* 277, 41311-7 (2002).
51. Muller, S., Hoege, C., Pyrowolakis, G. & Jentsch, S. SUMO, ubiquitin's mysterious cousin. *Nat Rev Mol Cell Biol* 2, 202-10 (2001).
52. Kirkpatrick, R. B., Matico, R. E., McNulty, D. E., Strickler, J. E. & Rosenberg, M. An abundantly secreted glycoprotein from *Drosophila melanogaster* is related to mammalian secretory proteins produced in rheumatoid tissues and by activated macrophages. *Gene* 153, 147-54 (1995).
53. Schneider, I. Cell lines derived from late embryonic stages of *Drosophila melanogaster. J Embyol Exp Morphol* 27, 353-65 (1972).
54. Boutros, M., Agaisse, H. & Perrimon, N. Sequential activation of signaling pathways during innate immune responses in *Drosophila. Dev Cell* 3, 711-22 (2002).
55. Ohshima, T., Koga, H. & Shimotohno, K. Transcriptional Activity of Peroxisome Proliferator-activated Receptor {gamma} Is Modulated by SUMO-1 Modification. *J Biol Chem* 279, 29551-29557 (2004).

What is claimed is:

1. A method of screening for a compound that regulates SUMOylation of a nuclear receptor protein comprising:
   a. contacting the compound of interest to the nuclear receptor protein, and
   b. detecting coupling of small ubiquitin-like modifier (SUMO) to the nuclear receptor protein, wherein the coupling of SUMO to the nuclear receptor protein in the presence of the compound of interest is indicative of the regulation of SUMOylation of the nuclear receptor protein by the compound of interest, wherein the nuclear receptor protein is selected from a group consisting of PPARγ, PPARα, PPARδ, LXRα and LXRβ, thereby screening for a compound that regulates SUMOylation of a nuclear receptor protein.

2. The method of claim 1, wherein the compound that regulates SUMOylation and inflammation and comprises a small molecule, a peptide, or a combination thereof.

3. The method of claim 1, wherein SUMOylation is detected using co-immunoprecipitation.

4. A method of assaying SUMOylation of nuclear receptor proteins comprising the steps of claim 1.

5. The method of claim 1, wherein SUMOylation is detected by assaying transcriptional activation of a reporter gene, two-hybrid screens, fluorescence resonance energy transfer (FRET), enzyme-linked immunosorbent assay (ELISA), co-immunoprecipitation, Western blotting or chromatin immunoprecipitation.

6. The method of claim 1, wherein the compound of interest induces SUMOylation of nuclear receptor proteins.

* * * * *